United States Patent [19]

Jirkovsky

[11] 4,409,224

[45] Oct. 11, 1983

[54] PYRIMIDO[1,6-A]INDOLE DERIVATIVES

[75] Inventor: Ivo L. Jirkovsky, Montreal, Canada

[73] Assignee: American Home Products Corp., New York, N.Y.

[21] Appl. No.: 282,575

[22] Filed: Jul. 13, 1981

Related U.S. Application Data

[62] Division of Ser. No. 941,816, Sep. 11, 1978, Pat. No. 4,307,234.

[51] Int. Cl.$^3$ ................. A61K 505/00; C07D 487/04; C07D 491/14; C07D 521/00
[52] U.S. Cl. ................................. 424/251; 424/244; 424/248.4; 424/248.52; 424/248.53; 424/248.56; 544/11; 544/96; 544/115; 544/116; 544/119; 544/245; 544/246; 544/247; 544/252; 260/243.3
[58] Field of Search ............... 544/252, 246, 116, 119; 260/243.3; 424/251, 248.4, 248.52

[56] References Cited

U.S. PATENT DOCUMENTS 3,649,626 3/1972 von Strandtmann et al. ...... 544/245
3,898,226 8/1975 Sulkowski ........................... 544/252

OTHER PUBLICATIONS

Borisova, et al., "Chemical Abstracts", vol. 74 (1971), Col. 22792Z.
Borisova, et al., "Chemical Abstracts", vol. 77 (1972), Col. 139850k.
Artemenko, et al., "Chemical Abstracts", vol. 86 (1977), Col. 37493q.
Cattarach, et al., "J. Chem. Soc. (C)", 1971, pp. 359–366.

Primary Examiner—Donald G. Daus
Assistant Examiner—James H. Turnipseed
Attorney, Agent, or Firm—Arthur E. Wilfond

[57] ABSTRACT

Pyrimido[1,6-a]indole derivatives characterized by having a substituted ethyl group at position 5 and optionally being further substituted at various positions on the pyrimido[1,6-a]indole nucleus are disclosed. The foregoing compounds are useful as antihypertensive agents in a mammal. Methods for their preparation also are disclosed.

35 Claims, No Drawings

PYRIMIDO[1,6-A]INDOLE DERIVATIVES

This is a division, of application Ser. No. 941,816, filed Sept. 11, 1978, now U.S. Pat. No. 4,307,234.

BACKGROUND OF THE INVENTION (a) Field of the Invention

This invention relates to novel pyrimido[1,6-a]indole derivatives, to therapeutically acceptable salts thereof, to processes for their preparation and to pharmaceutical compositions of the derivatives.

More specifically, the present invention relates to novel pyrimido[1,6-a]indole derivatives having a substituted ethyl group at position 5 and optionally being further substituted at various positions on the pyrimido[1,6-a]indole nucleus. These derivatives are useful as antihypertensive agents at dosages which do not elicit undesirable side effects.

(b) Description of the Prior Art

Only a limited number of reports dealing with compounds having a pyrimido[1,6-a]indole nucleus are available. More specifically, the reported pyrimido[1,6-a]indoles are substituted at positions 5 and 7 with a methyl group, see L. N. Borisova et al, Khim. Geterotsikl. Soedin., 645(1972) cf. Chem. Abstr., 77, 139850 k (1972), and C. J. Cattanach et al., J. Chem. Soc. (c), 359(1971). Other pyrimido[1,6-a]indole derivatives are also known; for example, 2,5-dimethyl-1,2,3,4-tetrahydropyrimido[1,6-a]indole derivatives and 2,5-dimethyl-4a,5-dihydropyrimido[1,6-a]indole derivatives are reported by G. N. Artemenko et al., Farmakol. Toksikol, 39, 651 (1976), cf. Chem. Abstr., 86, 37493 q (1977), to have antidepressant activity.

The compounds of the present invention are structurally different from the prior art compounds by having a substituted ethyl group at position 5 of the pyrimido[1,6-a]indole ring system.

SUMMARY OF THE INVENTION

The compounds of this invention are represented by formula I

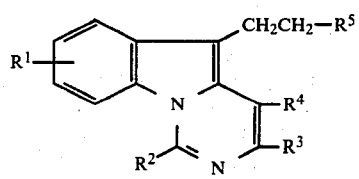

(1)

in which $R^1$ is hydrogen, lower alkyl, lower alkoxy, benzyloxy, lower alkanoyloxy, halo, nitro or trifluoromethyl;

$R^2$ is hydrogen, lower alkyl, cyclo(lower)alkyl, phenyl(lower)alkyl, phenyl, or a radical formula $-(CH_2)_h-NR^6R^7$ wherein h is an integer from 0 to 6, $R^6$ is lower alkyl and $R^7$ is hydrogen or lower alkyl or $R^6$ and $R^7$ together form a chain of formula $-(CH_2)_k-$ wherein k is an integer from 4 to 7;

$R^3$ is hydrogen, lower alkyl, benzyl, phenyl or a radical of formula $-NHCO-(CH_2)_2-CONR^8R^9$ wherein $R^8$ and $R^9$ each is lower alkyl or $R^8$ and $R^9$ together form a chain of formula $-(CH_2)_j-$ wherein j is an integer from 4 to 7;

$R^4$ is lower alkyl; or $R^3$ and $R^4$ together form a chain of formula $-(CH_2)_m-$ wherein m is an integer from 3 to 5; and $R^5$ is bromo, chloro, hydroxy, lower alkoxy or lower alkythio; or $R^5$ is a radical of formula $-S-CS-NR^{10}R^{11}$ wherein $R^{10}$ and $R^{11}$ each is lower alkyl or $R^{10}$ and $R^{11}$ together form a chain of formula $-(CH_2)_p-Y-(CH_2)_q-$ wherein p and q each is an integer from 1 to 3 and Y is $CH_2$, oxa or NH; or $R^5$ is a radical of formula $-X-C(=NR^{12})NHR^{13}$ wherein $R^{12}$ and $R^{13}$ each is hydrogen, lower alkyl or cyclo(lower)alkyl or $R^{12}$ and $R^{13}$ together form a chain of formula $-(CH_2)_r-$ wherein r is an integer from 2 to 4 and X is oxa or thia; or $R^5$ is a radical of formula $-NR^{14}R^{15}$ wherein $R^{14}$ and $R^{15}$ each is lower alkyl, lower alkenyl, lower alkynyl, cyclo(lower)alkyl, lower alkoxy(lower)alkyl or hydroxy(lower)alkyl; or $R^5$ is a radical of formula $-NR^{14}R^{15}$ wherein $R^{14}$ and $R^{15}$ together form a chain of the following type: $-(CH_2)_p-CH=CH-(CH_2)_q-$ wherein p and q are as defined herein, $-(CH_2)_p-Z-(CH_2)_q$ wherein p and q are defined herein and Z is oxa, $NR^{16}$ wherein $R^{16}$ is lower alkyl, lower alkoxy, phenyl or phenyl monosubstituted with lower alkyl or lower alkoxy, or $CHR^{17}$ wherein $R^{17}$ is hydrogen, lower alkyl, phenyl, benzyl, lower alkanoylamino or benzoylamino, $-CH_2CHR^{18}-Y-CHR^{19}CH_2-$ wherein $R^{18}$ and $R^{19}$ each is lower alkyl and Y is as defined herein, or $-CH=N-CH=CH-$.

A preferred group of compounds are represented by formula I in which $R^1$ is hydrogen, lower alkyl, lower alkoxy, halo, nitro or trifluoromethyl;

$R^2$ is hydrogen, lower alkyl, cyclo(lower)alkyl, phenyl(lower)alkyl, phenyl or a radical of formula $-(CH_2)_h-NR^6R^7$ wherein h is an integer from 0 to 6, $R^6$ is lower alkyl and $R^7$ is hydrogen or lower alkyl or $R^6$ and $R^7$ together form a chain of formula $-(CH_2)_k$ wherein k is an integer from 4 to 7;

$R^3$ is hydrogen, lower alkyl or a radical of formula $-NHCO-(CH_2)_2-CONR^8R^9$ wherein $R^8$ and $R^9$ each is lower alkyl or $R^8$ and $R^9$ together form a chain of formula $-(CH_2)_j-$ wherein j is an integer from 4 to 7;

$R^4$ is lower alkyl; and $R^5$ is bromo, chloro, hydroxy or lower alkoxy; or $R^5$ is a radical of formula $-S-CS-NR^{10}R^{11}$ wherein $R^{10}$ and $R^{11}$ each is lower alkyl or $R^{10}$ and $R^{11}$ together form a chain of formula $-(CH_2)_p-CH_2-(CH_2)_q-$ wherein p and q each is an integer from 1 to 3; or $R^5$ is a radical of formula $-X-C(=NR^{12})NHR^{13}$ wherein $R^{12}$ and $R^{13}$ together form a chain of formula $-(CH_2)_r-$ wherein r is an integer from 2 to 4 and X is oxa or thia; or $R^5$ is a radical of formula $-NR^{14}R^{15}$ wherein $R^{14}$ and $R^{15}$ each is lower alkyl, lower alkenyl, cyclo(lower)alkyl, hydroxy(lower)alkyl; or $R^5$ is a radical of formula $-NR^{14}R^{15}$ wherein $R^{14}$ and $R^{15}$ together form a chain of the following type: $-(CH_2)_p-CH=CH-(CH_2)_q-$ wherein p and q are as defined herein, $-(CH_2)_p-Z-(CH_2)_q-$ wherein p and q are as defined herein and Z is oxa, $NR^{16}$ wherein $R^{16}$ is lower alkyl, phenyl or phenyl monosubstituted with lower alkyl or lower alkoxy, or $CHR^{17}$ wherein $R^{17}$ is hydrogen, lower alkyl or benzoylamino, $-CH_2CHR^{18}-Y-CHR^{19}CH_2-$ wherein $R^{18}$ and $R^{19}$ each is lower alkyl and Y is $CH_2$, or

—CH=N—CH=CH—.

Another preferred group of compounds are represented by formula I in which $R^1$ is hydrogen; $R^2$ is lower alkyl, cyclo(lower)alkyl, pyrrolidin-1-ylmethyl or a radical of formula —$NR^6R^7$ wherein $R^6$ and $R^7$ each is lower alkyl; $R^3$ is hydrogen, lower alkyl or [4-(pyrrolidin-1-yl)-1,4-dioxobutyl]amino; $R^4$ is lower alkyl; and $R^5$ is bromo, chloro, lower alkoxy, 1-pyrrolidinylthioxomethylthio, 4,5-dihydro-1H-imidazol-2-ylthio, or a radical of formula —$NR^{14}R^{15}$ wherein $R^{14}$ is lower alkyl and $R^{15}$ is lower alkyl, or hydroxy(lower)alkyl, or $R^{14}$ and $R^{15}$ together form a chain of formula —$CH_2CH=CH$—$(CH_2)_2$—, —$(CH_2)_2$—O—$(CH_2)_2$—, —$(CH_2)_4$—, —$(CH_2)_5$—, —$(CH_2)_2$—$NR^{16}$—$(CH_2)_2$— wherein $R^{16}$ is lower alkyl or 4-(lower alkoxy)phenyl, —$(CH_2)_2$—$CHR^{17}$—$(CH_2)_2$— wherein $R^{17}$ is benzoylamino, —$CH_2CHR^{18}CH_2CHR^{19}CH_2$— wherein $R^{18}$ and $R^{19}$ each is lower alkyl, or —CH=N—CH=CH—.

A most preferred group of compounds are represented by formula I in which $R^1$ and $R^3$ are hydrogen; $R^2$ is lower alkyl, cyclo(lower)alkyl or pyrrolidin-1-ylmethyl; $R^4$ is lower alkyl; and $R^5$ is a radical of formula —$NR^{14}R^{15}$ wherein $R^{14}$ and $R^{15}$ each is lower alkyl or $R^{14}$ and $R^{15}$ together form a chain of formula —$CH_2CH=CH$—$(CH_2)_2$—, —$(CH_2)_2$—O—$(CH_2)_2$—, —$(CH_2)_4$—, —$(CH_2)_5$—, —$(CH_2)_2NR^{16}$—$(CH_2)_2$— wherein $R^{16}$ is lower alkyl or 4-(lower alkoxy)phenyl, or —$(CH_2)_2$—$CHR^{17}$—$(CH_2)_2$— wherein $R^{17}$ is benzoylamino.

The therapeutically acceptable acid addition salts of the compounds of formula I are included within the scope of this invention.

The compounds of this invention are useful for treating hypertension in a mammal by administering to the mammal an effective antihypertensive amount of a compound of formula I or a therapeutically acceptable acid addition salt thereof.

The compounds of this invention form a pharmaceutical composition which comprises a compound of formula I, or a therapeutically acceptable acid addition salt thereof, and a pharmaceutically acceptable carrier.

DETAILED DESCRIPTION OF THE INVENTION

The term "lower alkyl" as used herein means straight chain alkyl radicals containing from one to six carbon atoms and branched chain alkyl radicals containing three or four carbon atoms and includes methyl, ethyl, propyl, butyl, isobutyl, pentyl, hexyl and the like.

The term "lower alkoxy" as used herein means straight chain alkoxy radicals containing from one to six carbon atoms and branched chain alkoxy radicals containing three or four carbon atoms and includes methoxy, ethoxy, isopropoxy, butoxy, hexyloxy and the like.

The term "cyclo(lower)alkyl" as used herein means saturated cyclic hydrocarbon radicals containing from three to six carbon atoms and includes cyclopropyl, cyclobutyl, cyclopentyl and cyclohexyl.

The term "lower alkanol" as used herein means both straight and branched chain alkanols containing from one to four carbon atoms and includes methanol, ethanol, isopropanol, butanol and the like.

The term "lower alkanoyl" as used herein means straight chain alkanoyl radicals containing from two to six carbon atoms and a branched chain alkanoyl radical containing four carbon atoms and includes acetyl, 1-oxopropyl, 1-oxo-2-methylpropyl, 1-oxohexyl and the like.

The term "lower alkenyl" as used herein means straight chain alkenyl radicals containing from two to six carbon atoms and branched chain alkenyl radicals containing three or four carbon atoms and includes ethenyl, 2-methyl-2-propenyl, 4-hexenyl and the like.

The term "lower alkynyl" as used herein means straight chain alkynyl radicals containing from two to six carbon atoms and a branched chain alkynyl radical containing four carbon atoms and includes ethynyl, 2-propynyl, 1-methyl-2-propynyl, 3-hexynyl and the like.

The term "halo" as used herein means halogens and includes fluorine, chlorine, bromine and iodine, unless stated otherwise.

The term "organic proton acceptor" as used herein means the organic bases, or amines for instance, triethylamine, pyridine, N-ethylmorpholine, 1,5-diazabicyclo[4.3.0]non-5-ene and the like.

The term "inorganic proton acceptor" as used herein means the inorganic bases, preferably the alkali metal hydroxides, carbonates and bicarbonates, for example, sodium hydroxide, potassium hydroxide, sodium carbonate, sodium bicarbonate, potassium carbonate and the like.

The term "proton acceptor" as used herein means a proton acceptor selected from an organic proton acceptor and inorganic proton acceptor, as defined herein.

Also included in this invention are the possible stereochemical isomers of the compounds of formula I. Such isomers can be obtained in substantially pure form by classical separation techniques and by sterically controlled synthesis. Individual enantiomers, which might be separated by fractional crystallization of the diastereomeric salts thereof, are also included.

The term "therapeutically acceptable addition salt" as used herein includes the therapeutically acceptable acid addition salts of the compound of formula I. The acid addition salts are prepared by reacting the base form of the appropriate compound of formula I with one or more equivalents, preferably with an excess, of the appropriate acid in an organic solvent, for example, diethyl ether or an ethanol-diethyl ether mixture. These salts, when administered to a mammal, possess the same pharmacologic activities as the corresponding base. For many purposes it is preferable to administer the salts rather than the base compounds. Suitable acids to form these salts include the common mineral acids, for instance, hydrobromic, hydrochloric, sulfuric or phosphoric acid; as well as the organic acids, for instance, formic, acetic, maleic, fumaric, citric, or tartaric acid; or acids which are sparingly soluble in body fluids and which impart slow-release properties to their respective salts such as pamoic or tannic acid or carboxymethyl cellulose. The addition salts thus obtained are the functional equivalent of the parent base compound in respect to their therapeutic use. Hence, these addition salts are included within the scope of this invention and are limited only by the requirement that the acids employed in forming the salts be therapeutically acceptable.

The antihypertensive effect of the compounds of formula I or therapeutically acceptable acid addition salts thereof is demonstrated in standard pharmacological tests, for example, in tests conducted in the spontaneously hypertensive rat (SHR) such as described by I. Vavra, et al., Can. J. Physiol. Pharmacol., 51, 727(1973).

More specifically exemplified, the compounds of formula I are shown to be effective antihypertensive agents by using the testing method described in the latter publication. The latter test method is modified so that the test compound is administered to the rat by gastric gavage and the systolic blood pressure is measured by the tailcuff method before administration of the compound and 4 hours thereafter. The following representative compounds of formula I reduce the systolic blood pressure by at least 15% (the amount of test compound to cause this reduction in blood pressure is indicated in the parentheses):

S-(4,5-dihydro-1H-imidazol-2-yl)-1,4-dimethylpyrimido[1,6-a]indole-5-ethanethiol dihydrochloride (50 mg/kg, described in Example 21), N-(1-methylethyl)-1,4,N-trimethylpyrimido[1,6-a]indole-5-ethanamine dihydrochloride (5 mg/Kg, described in Example 22), 1-cyclohexyl-4-methyl-5-[2-(1-pyrrolidinyl)ethyl]pyrimido[1,6-a]indole dihydrochloride (2.5 mg/Kg, described in Example 31), 1,4-dimethyl-5-[2-(1-piperidinyl)ethyl]-pyrimido[1,6-a]indole dihydrochloride (50 mg/Kg, described in Example 25), 4-methyl-5-[2-(1-piperidinyl)ethyl]-1-propylpyrimido[1,6-a]indole dihydrochloride (10 mg/Kg, described in Example 32), 1,4-dimethyl-5-[2-(1-pyrrolidinyl)ethyl]-pyrimido[1,6-a]indole dihydrochloride (25 mg/Kg, described in Example 25), 1,4-dimethyl-5-[2-(4-morpholinyl)ethyl]pyrimido[1,6-a]-indole dihydrochloride (50 mg/Kg, described in Example 25), 1,4-dimethyl-5-[2-[4-(4-methoxyphenyl)-1-piperazinyl]ethyl]pyrimido[1,6-a]indole dihydrochloride (10 mg/Kg, described in Example 27), and 4-methyl-5-[2-(1-pyrrolidinyl)ethyl]-1-[(1-pyrrolidinyl)methyl]pyrimido[1,6-a]indole dihydrochloride (10 mg/Kg, described in Example 35).

When the compounds of formula I of this invention are used as antihypertensive agents in mammals, e.g. rats, dogs and mice, they are used alone or in combination with pharmacologically acceptable carriers, the proportion of which is determined by the solubility and chemical nature of the compound, chosen route of administration and standard biological practice. For example, they are administered orally in solid form, i.e. capsule or tablet. They can also be administered orally in the form of suspensions or solutions or they may be injected parenterally. For parenteral administration they can be used in the form of a sterile solution containing other solutes, for example enough saline or glucose to make the solution isotonic.

The tablet compositions contain the active ingredient in admixture with nontoxic pharmaceutical excipients are, for example, starch, milk, sugar, certain types of clay and so forth. The tablets can be uncoated or they can be coated by known techniques so as to delay disintegration and adsorption in the gastrointestinal tract and thereby provide a sustained action over a longer period.

The aqueous suspensions of the compounds of formula I contain the active ingredient in admixture with one or more non-toxic pharmaceutical excipients known to be suitable in the manufacture of aqueous suspensions. Suitable excipients are, for example, methylcellulose, sodium alginate, gum acacia, lecithin and so forth. The aqueous suspensions can also contain one or more preservatives, one or more colouring agents, one or more flavouring agents and one or more sweetening agents.

Non-aqueous suspensions can be formulated by suspending the active ingredient in a vegetable oil, for example, arachis oil, olive oil, sesame oil, or coconut oil, or in a mineral oil, for example, liquid paraffin, and the suspension may contain a thickening agent, for example, beeswax, hard paraffin or cetyl alcohol. These compositions can also contain a sweetening agent, flavouring agent or antioxidant.

The dosage of the compounds of formula I as antihypertensive agents will vary with the form of administration and the particular compound chosen. Furthermore, it will vary with the particular host as well as the age and condition of the host under treatment. Generally, treatment is initiated with small dosages substantially less than the optimum dose of the compound. Thereafter, the dosage is increased by small increments until the optimum effect under circumstances is reached. In general, the compounds of this invention are most desirably administered at a concentration level that will generally afford effective results without causing any harmful or deleterious side effects. The effective antihypertensive amount of the compounds usually ranges from about 0.1 mg to about 300 mg per kilogram body weight per day, although as aforementioned variations will occur. However, a dosage level that is in the range from about 0.5 mg to about 100 mg per kilogram body weight per day is employed most desirably in order to achieve effective results.

The compound of formula I, or a therapeutically acceptable salt thereof, also can be used to produce beneficial effects in the treatment of hypertension, peripheral and cerebral vascular diseases and related disorders when combined with a therapeutically effective amount of a diuretic and/or antihypertensive agent commonly used in antihypertensive therapy. Such antihypertensive therapeutic agents include, for example, the thiazide diuretics for instance, chlorothiazide or hydrochlorothiazide; mineralocorticoid antagonizing diuretic agents, e.g., spironolactone; and other diuretics such as triamterene and furosemide. Examples of still other suitable antihypertensive agents are prazosin, hydralazine and centrally active antihypertensive agents such as methyldopa, clonidine, and reserpine; as well as the $\beta$-adrenergic blocking agents, for instance, propranolol. In this instance, the compound of formula I, or its therapeutically acceptable acid addition salt can be administered sequentially or simultaneously with the antihypertensive and/or diuretic agent. Preferred antihypertensive therapeutic agents are the antihypertensive agents such as the thiazides, mineralocorticoid antagonizing diuretic agents and the $\beta$-adrenergic blocking agents. A combination of the foregoing antihypertensive and/or diuretic agents, e.g. propranolol and hydrochlorothiazide, can be substituted for a single agent. Suitable methods of administration, compositions and dosages of the above described diuretic and/or antihypertensive agents are described in medical textbooks; for instance, "Physicians' Desk Reference", 32 ed., Medical Economics Co., Oradell, N.J., U.S.A., 1978; thus for example, the agent propranolol is administered daily to humans in a range of 80 to 640 mg, usually in the form of unit doses of 10, 20, 40 or 80 mg. When used in combination, the compound of formula I, or its therapeutically acceptable salt is administered as described previously.

chloride of formula $R^2$—COCl in the presence of 1.1 to 2.0 molar equivalents of an organic proton acceptor, preferably triethylamine or N-ethylmorpholine, in an inert organic solvent, preferably tetrahydrofuran, dioxane, dimethylformamide, diethyl ether or ethyl acetate, is stirred at 0° to 50° C. for 10 to 50 hours and the corresponding compound of formula II is isolated.

Cyclization of the compound of formula II gives the corresponding compound of formula I in which $R^5$ is bromo, chloro or hydroxy. This cyclization can be achieved in a single reaction step or in two reaction steps through an intermediate of formula VI and is illustrated in reaction Scheme 2.

the corresponding compound of formula VI and at a temperature of 60° to 160° C., preferably 65° to 120° C. for 0.5 to three hours gives the corresponding compound of formula I in which $R^5$ is bromo.

When the compound of formula VI is required, a minimum of about 1.1 to 2.0 molar equivalents of the dehydrating agent is used and when the compound of formula I is required, a minimum of 3, preferably 3 to 10 molar equivalents of the dehydrating agent is used, however, large excesses of the dehydrating agent can be used in both cases without detrimental effects. The above dehydration reactions can be conducted in an inert organic solvent, preferred solvents can be selected Reaction Scheme 2

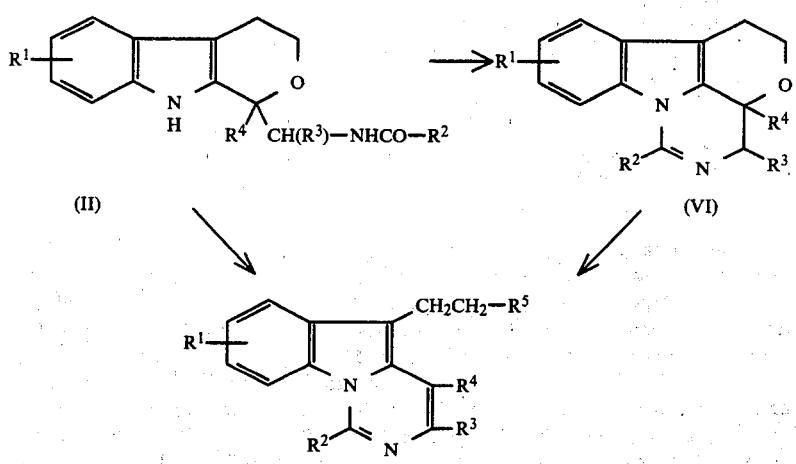

(1) in which $R^5$ is bromo, chloro or hydroxy.

With reference to reaction Scheme 2, reaction of the compound of formula II with a dehydrating agent gives the corresponding compound of formula I or VI.

A number of dehydrating agents can be used, for example, phosphorus oxychloride, phosphorus tribromide, phosphorus pentachloride and polyphosphoric acid. Phosphorus oxychloride and phosphorus tribromide are the preferred agents. Furthermore, a particular dehydrating agent determines which compound of formula I will be formed: use of phosphorus oxychloride, phosphorus trichloride or phosphorus pentachloride affords the corresponding compound of formula I in which $R^5$ is chloro; use of phosphorus oxybromide or phosphorus tribromide affords the corresponding compound of formula I in which $R^5$ is bromo; and use of polyphosphoric acid affords the corresponding compound of formula I in which $R^5$ is hydroxy.

The temperature of this dehydration reaction determines the formation of either the compound of formula I or the compound of formula VI. When using phosphorus oxychloride, phosphorus pentachloride or polyphosphoric acid as dehydrating agent, a temperature range of 50° to 110° C., preferably 80° to 100° C., for 30 to 150 minutes allows the formation and subsequent isolation of the corresponding compound of formula VI and a temperature range of 120° to 200° C., preferably 130° to 160° C., for 0.5 to three hours gives the corresponding compound of formula I. Use of phosphorus tribromide at 40° to 55° C., for 30 to 150 minutes gives from chloroform, benzene, toluene or xylene. However, if a sufficient amount of the dehydrating agent is used, the dehydration reaction can be conducted without a solvent.

Reaction of the compound of formula VI with a minimum of 1.1 molar equivalents preferably 1.5 to 3 molar equivalents, of the dehydrating agent in the same manner as described above for the preparation of the compound of formula I, affords the corresponding compound of formula I in which $R^5$ is bromo, chloro or hydroxy.

Although the compound of formula I in which $R^5$ is hydroxy can be obtained using polyphosphoric acid in the manner described above, the latter compound of formula I can also be obtained from the corresponding compound of formula I in which $R^5$ is bromo or chloro by alkaline hydrolysis. For this hydrolysis, a mixture of the compound of formula I in which $R^5$ is chloro or bromo in a water immiscible organic solvent, preferably chloroform or methylene chloride, and a molar excess of an aqueous solution of sodium or potassium hydroxide (5 to 20% solution) is stirred at 30° to 60° C. for one to five hours and the corresponding compound of formula I in which $R^5$ is hydroxy is isolated from the organic phase of the reaction mixture.

The compound of formula I in which $R^2$ is a radical of formula —$(CH_2)_n$—$NR^6R^7$ wherein n is an integer from 1 to 6, and $R^6$ and $R^7$ are as defined herein also can be prepared via the sequence of reactions illustrated by Scheme 3.

Reaction Scheme 3

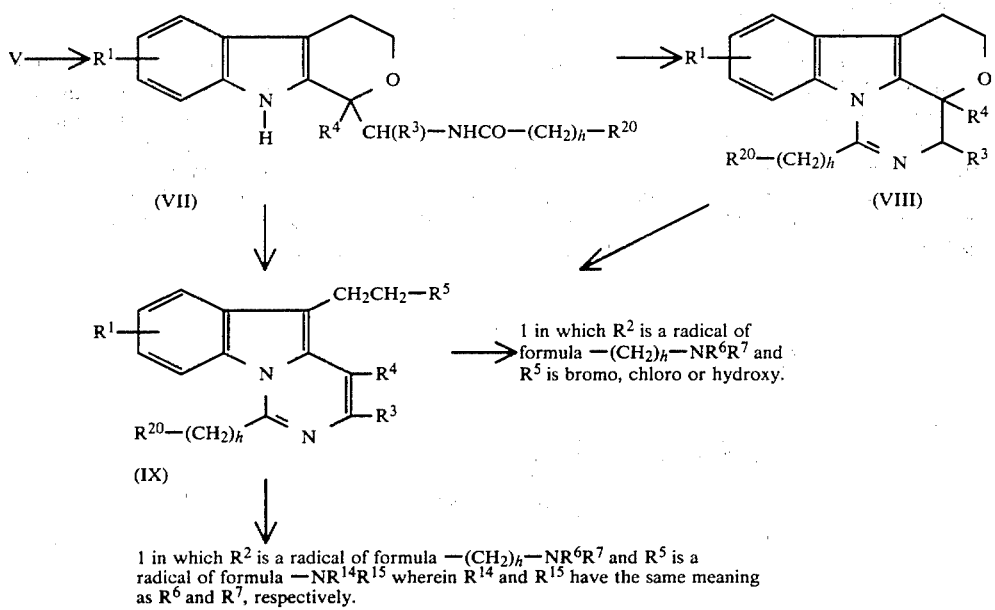

1 in which $R^2$ is a radical of formula $-(CH_2)_h-NR^6R^7$ and $R^5$ is a radical of formula $-NR^{14}R^{15}$ wherein $R^{14}$ and $R^{15}$ have the same meaning as $R^6$ and $R^7$, respectively.

With reference to reaction scheme 3, the primary amine of formula V is condensed with an acid chloride of formula $ClCO-(CH_2)_h-R^{20}$ in which h is an integer from 1 to 6, and $R^{20}$ is chloro or bromo, in the same manner as described above for the condensation of the primary amine of formula V and the acid chloride of formula $R^2-COCl$, to obtain the corresponding compound of formula VII in which $R^1$ and $R^4$ are as defined herein, $R^3$ is hydrogen, lower alkyl, benzyl or phenyl, or $R^3$ and $R^4$ together form a chain of formula $-(CH_2)_m-$ wherein m is as defined herein, h is an integer from 1 to 6 and $R^{20}$ is chloro or bromo. Cyclization of the latter compound of formula VII with a dehydrating agent, in the same manner as described above for the reaction sequence II→I, II→VI and VI→I, gives the corresponding compound of formula VIII wherein $R^1$, $R^3$, $R^4$, h and $R^{20}$ are as defined immediately above and the corresponding compound of formula IX wherein $R^1$, $R^3$, $R^4$, h and $R^{20}$ are as defined immediately above and $R^5$ is bromo, chloro or hydroxy.

Condensation of the compound of formula IX with 1.0 to 1.3 molar equivalents of an amine of formula $HNR^6R^7$ in the presence of a proton acceptor, for example, sodium bicarbonate, triethylamine or N-ethylmorpholine, preferably sodium bicarbonate, in an inert organic, preferably acetonitrile, gives the corresponding compound of formula I in which $R^1$, $R^3$ and $R^4$ are as defined immediately above, $R^2$ is a radical of formula $(CH_2)_h-NR^6R^7$ wherein h is an integer from 1 to 6, and $R^6$ and $R^7$ are as defined herein and $R^5$ is bromo, chloro or hydroxy. For this condensation, the reaction mixture is maintained at 30° to 50° C. for one to five hours and the compound of formula I is isolated.

Condensation of the compound of formula IX with two or more molar equivalents of the amine of formula $HNR^6R^7$ in the presence of an organic proton acceptor at elevated temperatures gives the corresponding compound of formula I in which $R^1$, $R^3$ and $R^4$ are as defined immediately above, $R^2$ is a radical of formula $(CH_2)_h-NR^6R^7$ wherein h is an integer from 1 to 6, and $R^6$ and $R^7$ are as defined herein and $R^5$ is a radical of formula $-NR^{14}R^{15}$ wherein $R^{14}$ and $R^{15}$ have the same meaning as $R^6$ and $R^7$, respectively. For this condensation, the reaction mixture is maintained at 50° to 100° C. for 5 to 20 hours and the reaction can be conducted in an inert organic solvent, for example, benzene, toluene or acetonitrile, or an excess of the amine of formula $HNR^6R^7$ can serve as the solvent. Suitable organic proton acceptors can be selected from two or more equivalents of triethylamine, N-ethylmorpholine or the amine of formula $HNR^6R^7$.

If desired, the above described compounds of formula I in which $R^1$, $R^2$ and $R^4$ are as defined herein; $R^3$ is hydrogen, lower alkyl, benzyl or phenyl; or $R^3$ and $R^4$ together form a chain of formula $-(CH_2)_m-$ wherein m is as defined herein; and $R^5$ is bromo, chloro or hydroxy can be converted to other compounds of formula I in which $R^1$, $R^2$, $R^3$, $R^4$ and $R^5$ are as defined herein by methods described hereinafter.

In one conversion, the compound of formula I in which $R^1$, $R^2$ and $R^4$ are as defined herein, $R^3$ is hydrogen and $R^5$ is hydroxy is reacted with 5 to 20 molar equivalents of N-bromosuccinimide and potassium carbonate in an inert organic solvent, preferably chloroform, at 50° to 70° C. for 30 to 100 minutes to obtain the corresponding intermediate having the 2,5-dioxopyrrolidin-1-yl group at position 3 of the pyrimido[1,6-a]indole nucleus. Reaction of the latter intermediate with 1.1 to 3.0 molar equivalents of an amine of formula $HNR^8R^9$ wherein $R^8$ and $R^9$ are as defined herein at 70° to 90° C. for 4 to 10 hours gives the corresponding compound of formula I in which $R^1$, $R^2$ and $R^4$ are as defined herein, $R^3$ is a radical of formula $NHCO-(CH_2)_2-CONR^8R^9$ wherein $R^8$ and $R^9$ are as defined herein and $R^5$ is hydroxy. A solvent can be omitted from the latter reaction if the reactants are mutually soluble, otherwise an inert organic solvent can be employed, for example, benzene, toluene, dimethylformamide or acetonitrile. Reaction of the latter compound of formula I with 1.2 to 2.0 molar equivalents of thionyl bromide or thionyl chloride in an inert organic solvent, preferably chloroform, benzene or toluene, at 50° to 100° C. for one to six hours affords the corresponding compound of formula I in which $R^1$, $R^2$ and $R^4$ are as defined herein, $R^3$ is a radical of formula NHCO—$(CH_2)_2$—$CONR^8R^9$ wherein $R^8$ and $R^9$ are as defined herein and $R^5$ is bromo or chloro.

Repeating the above conversion but condensing the compound of formula I in which $R^1$, $R^2$ and $R^4$ are as defined herein, $R^3$ is hydrogen and $R^5$ is bromo or chloro with N-bromosuccinimide, in the same manner as described above, followed by reacting the resulting intermediate with 2.5 to 5.0 molar equivalents of the amine of formula $HNR^8R^9$ wherein $R^8$ and $R^9$ are as defined herein, in the same manner as described above, gives the corresponding compound of formula I in which $R^1$, $R^2$ and $R^4$ are as defined herein, $R^3$ is a radical of formula NHCO—$(CH_2)_2$—$CONR^8R^9$ wherein $R^8$ and $R^9$ are as defined herein and $R^5$ is a radical of formula $NR^{14}R^{15}$ wherein $R^{14}$ and $R^{15}$ have the same meaning as $R^8$ and $R^9$, respectively.

Reaction of the compound of formula I in which $R^1$, $R^2$, $R^3$ and $R^4$ are as defined herein and $R^5$ is bromo or chloro with 1.0 to 1.2 molar equivalents of sodium in a minimum of 2 molar equivalents of a lower alkanol or a lower alkylthiol at 50° to 100° C. gives the corresponding compound of formula I in which $R^1$, $R^2$, $R^3$ and $R^4$ are as defined herein and $R^5$ is lower alkoxy or lower alkylthio.

In another conversion, the compound of formula I in which $R^1$, $R^2$, $R^3$ and $R^4$ are as defined herein and $R^5$ is bromo or chloro and 1.0 to 1.2 molar equivalents of a compound of formula $NaSCSNR^{10}R^{11}$ wherein $R^{10}$ and $R^{11}$ each is lower alkyl or $R^{10}$ and $R^{11}$ together form a chain of formula —$(CH_2)_p$—Y—$(CH_2)_q$— wherein p, q and Y are as defined herein in an inert solvent, preferably a mixture of a lower alkanol and water is heated at 70° to 120° C. for 10 to 30 hours to obtain the corresponding compound of formula I in which $R^1$, $R^2$, $R^3$ and $R^4$ are as defined herein and $R^5$ is a radical of formula —S—CS—$NR^{10}R^{11}$ wherein $R^{10}$ and $R^{11}$ are as defined herein.

Condensation of the compound of formula I in which $R^1$, $R^2$, $R^3$ and $R^4$ are as defined herein and $R^5$ is bromo or chloro with 1.1 to 2.0 molar equivalents of a compound of formula X=$C(NHR^{12})NHR^{13}$ wherein X, $R^{12}$ and $R^{13}$ are as defined herein in an anhydrous inert organic solvent, preferably tetrahydrofuran or dioxane, at 60° to 120° C. for 2 to 15 hours gives the corresponding compound of formula I in which $R^1$, $R^2$, $R^3$ and $R^4$ are as defined herein and $R^5$ is a radical of formula —X—C(=$NR^{12}$)$NHR^{13}$ wherein $R^{12}$, $R^{13}$ and X are as defined herein.

In still another conversion, the compound of formula I in which $R^1$, $R^2$, $R^3$ and $R^4$ are as defined herein and $R^5$ is bromo or chloro is condensed with a minimum of one molar equivalent of an amine of formula $HNR^{14}R^{15}$ wherein $R^{14}$ and $R^{15}$ are as defined herein in the presence of a minimum of one molar equivalent of a proton acceptor to obtain the coresponding compound of formula I in which $R^1$, $R^2$, $R^3$ and $R^4$ are as defined herein and $R^5$ is a radical of formula —$NR^{14}R^{15}$ wherein $R^{14}$ and $R^{15}$ are as defined herein. For this condensation, suitable proton acceptors can be selected from an inorganic proton acceptor, for example, a hydroxide, carbonate or bicarbonate of potassium or sodium, or an organic proton acceptor, for example, pyridine, triethylamine, N-ethylmorpholine or N-methylpiperidine, or an excess of the amine of formula $HNR^{14}R^{15}$ can serve as the proton acceptor. This condensation can be conducted in an inert solvent, for example, water, lower alkanol, tetrahydrofuran, dioxane, acetonitrile, chloroform, dimethylformamide, dimethyl sulfoxide, an excess of the amine of formula $HNR^{14}R^{15}$ or a mixture of these solvents. Usually the condensation reaction mixture is maintained at 50° to 200° C., preferably 60° to 120° C., for 15 minutes to 30 hours or until the condensation is complete.

The following examples illustrate further this invention.

EXAMPLE 1

N-[(1,3,4,9-Tetrahydro-1-methylpyrano[3,4-b]indol-1-yl)methyl]-acetamide (IIa; $R^1$ and $R^3$=H, $R^4$ and Alk=Me)

A solution of indole-3-ethanol (3.86 g) and N-(2-oxopropyl)-acetamide[3.0 g, described by R. H. Wiley and O. H. Borum, J.Amer.Chem. Soc., 70, 2005(1948)] in dry benzene (300 ml) is refluxed using a water separating condenser (Dean-Stark) until the water is removed. Boron trifluoride-etherate (5 drops) is added. The solution is refluxed using the water separating condenser for 30 minutes, stirred at 20° to 30° C. for 16 to 20 hours and evaporated. The residue is dissolved in chloroform and the solution is washed with 10% aqueous sodium bicarbonate, water and brine, dried over magnesium sulfate and evaporated. The residue is crystallized from benzene to obtain crystals (6.55 g) of the title compound solvated with one molar amount of benzene, mp 100°–102° C.

Anal: Calculated for $C_{15}H_{18}N_2O_2.C_6H_6$: C,74.97; H,7.19; N,8.33% Found: C,74.74; H,7.27; N,8.38%

In the same manner but replacing indole-3-ethanol with an equivalent amount of 7-ethylindole-3-ethanol, 6-methoxyindole-3-ethanol or 5-phenylmethoxy-indole-3-ethanol, the following compounds of formula IIa are obtained, respectively: N-[(8-ethyl-1,3,4,9-tetrahydro-1-methylpyrano[3,4-b]indol-1-yl)methyl]-acetamide, N-[(7-methoxy-1,3,4,9-tetrahydro-1-methylpyrano-[3,4-b]indol-1-yl)methyl]-acetamide and N-[(6-phenylmethoxy-1,3,4,9-tetrahydro-1-methylpyrano[3,4-b]indol-1-yl)methyl]-acetamide.

EXAMPLE 1 (Continued)

Similarly, replacing N-(2-oxopropyl)-acetamide with an equivalent amount of N-(2-oxopentyl)-acetamide, N-(1-ethyl-2-oxobutyl)-acetamide, N-(1-phenyl-2-oxobutyl)-propionamide or N-(1-benzyl-2-oxohexyl)-acetamide, the following compounds of formula IIa are obtained, respectively: N-[(1-propyl-1,3,4,9-tetrahydropyrano[3,4-b]indol-1-yl)methyl]-acetamide, N-[1-(1-ethyl-1,3,4,9-tetrahydropyrano[3,4-b]indol-1-yl)propyl]-acetamide, N-[(1-ethyl-1,3,4,9-tetrahydropyrano[3,4-b]indol-1-yl)phenylmethyl]-propionamide and N-[1-(1-butyl-1,3,4,9-tetrahydropyrano[3,4-b]indol-1-yl)-2-phenylethyl]-acetamide.

EXAMPLE 2

N-[1-(1,3,4,9-Tetrahydro-1-methylpyrano[3,4-b]indol-1-yl)ethyl]acetamide(IIa, $R^1$=H and $R^3$, $R^4$ and Alk=Me)

A mixture of indole-3-ethanol (16.1 g), benzene (1200 ml), N-(1-methyl-2-oxopropyl)-acetamide[12.7 g, described by A. Triebs and W. Sutter, Chem. Ber. 84, 96(1951)] and boron trifluoride-etherate (5 drops) is refluxed using a water separating condenser for 60 minutes. After cooling, the mixture is washed with concentrated sodium bicarbonate, dried over magnesium sulfate and evaporated. The residue is chromatographed on silica gel using chloroform. The eluates are evaporated to give a residue of the title compound as a 1:1 mixture of diastereoisomers:

ir(CHCl$_3$) 3450, 3415, 3250 and 1655 cm$^{-1}$; nmr(CDCl$_3$) δ0.88(d), 1.32(d), 1.53(s), 1.56(s), 1.68(s), 2.12(s), 9.52(s) and 10.40(s).

In the same manner but replacing indole-3-ethanol with an equivalent amount of 5-chloroindole-3-ethanol, 5-nitroindole-3-ethanol or 4-trifluoromethylindole-3-ethanol, the following compounds of formula IIa are obtained, respectively: N-[1-(6-chloro-1,3,4,9-tetrahydro-1-methylpyrano[3,4-b]indol-1-yl)ethyl]-acetamide, N-[1-(6-nitro-1,3,4,9-tetrahydro-1-methylpyrano[3,4-b]indol-1-yl)ethyl]-acetamide, and N-[1-(5-trifluoromethyl-1,3,4,9-tetrahydro-1-methyl-pyrano[3,4-b]indol-1-yl)ethyl]-acetamide.

EXAMPLE 3

1,3,4,9-Tetrahydro-1-methylpyrano[3,4-b]indole-1-methanamine (V; R$^1$ and R$^3$=H and R$^4$=Me)

A mixture of N-[(1,3,4,9-tetrahydro-1-methylpyrano[3,4-b]indol-1-yl)methyl]-acetamide (5.0 g, described in Example 1), in ethanol (200 ml) and 35% aqueous sodium hydroxide (45 ml) is refluxed overnight and evaporated to about 30 ml. Water and chloroform are added. The organic phase is washed successively with water and saturated brine solution, filtered through anhydrous magnesium sulfate and evaporated to give a residue (4.0 g) of the title compound, ir(CHCl$_3$)3465, 3400, 3180, 2930, 2870, 1450, 1295, 1080 and 1050 cm$^{-1}$.

In the same manner but replacing N-[(1,3,4,9-tetrahydro-1-methylpyrano[3,4-b]indol-1-yl)methyl]-acetamide with an equivalent amount of another compound of formula IIa described in Examples 1 and 2, the following compounds of formula V are obtained: respectively: 8-ethyl-1,3,4,9-tetrahydro-1-methylpyrano[3,4-b]indole-1-methanamine, 7-methoxy-1,3,4,9-tetrahydro-1-methylpyrano[3,4-b]indole-1-methanamine, 6-phenylmethoxy-1,3,4,9-tetrahydro-1-methylpyrano[3,4-b]indole-1-methanamine, 1-propyl-1,3,4,9-tetrahydropyrano[3,4-b]indole-1-methanamine, 1-(1-ethyl-1,3,4,9-tetrahydropyrano[3,4-b]indol-1-yl)propanamine,α-(1-ethyl-1,3,4,9-tetrahydropyrano[3,4-b]indol-1-yl)-benzenemethanamine, α-(1-butyl-1,3,4,9-tetrahydropyrano[3,4-b]indole-1-yl)-benzeneethanamine,1-(6-chloro-1,3,4,9-tetrahydro-1-methylpyrano[3,4-b]indol-1-yl)-ethanamine,1-(6-nitro-1,3,4,9-tetrahydro-1-methylpyrano[3,4-b]indol-1-yl)ethanamine and 1-(5-trifluoromethyl-1,3,4,9-tetrahydro-1-methylpyrano[3,4-b]indol-1-yl)-ethanamine.

EXAMPLE 4

N-[1,3,4,9-Tetrahydro-1-methylpyrano[3,4-b]indol-1-yl)methyl]-formamide (II; R$^1$, R$^2$ and R$^3$=H and R$^4$=Me)

98% Formic acid (23 g) is added to acetic anhydride (55 g) at 0° C. over 5 minutes. The resultant mixture is heated at 50° C. for 15 minutes, and then rapidly cooled down to 0° C. Seven ml of this prepared reagent is added at 0° C. (over 30 minutes) to a solution of 1,3,4,9-tetrahydro-1-methyl-pyrano[3,4-b]indole-1-methanamine (4.2 g, described in Example 3) in dry pyridine (40 ml). The reaction mixture is stirred at 20° to 27° C. for 24 hours and evaporated. The organic phase is washed with 5% sodium bicarbonate, dried over magnesium sulfate, filtered, and evaporated. The residue is crystallized from diethyl ether-hexane to obtain the title compound: mp 144° C.; ir(CHCl$_3$) 3420, 3260 and 1680 cm$^{-1}$; nmr (CDCl$_3$) δ6.00(broad), 7.80(broad siglet) and 9.45(siglet).

EXAMPLE 5

N-[(1,3,4,9-Tetrahydro-1-methylpyrano[3,4-b]indol-1-yl)methyl]-butanamide (II; R$^1$ and R$^3$=H, R$^2$=Pr and R$^4$=Me)

Butanoyl chloride (5.3 g) is added to a stirring mixture at 0° C. of 1,3,4,9-tetrahydro-1-methylpyrano[3,4-b]indole-1-methanamine (10.0 g, described in Example 3), triethylamine (5 g) and dry tetrahydrofuran (400 ml). The temperature is allowed to rise to room temperature, the reaction mixture is filtered, and the filtrate is evaporated to give the title compound (12.5 g): ir(CHCl$_3$) 3420, 3250, 2855 and 1660 cm$^{-1}$; nmr(CDCl$_3$) δ0.75(t), 1.57(s), 1.62(m), 2.08(t), 2.87(m), 3.91(t), 4.10(t), 6.12(s), 7.0–7.7(m) and 9.86(s)

In the same manner but replacing butanoyl chloride with an equivalent amount of 3-methylbutanoyl chloride, heptanoyl chloride, cyclopentyl-carbonyl chloride or benzenepropanoyl chloride, the following compounds of formula II are obtained, respectively: N-[(1,3,4,9-tetrahydro-1-methylpyrano[3,4-b]indol-1-yl)methyl]-3-methylbutanamide, N-[(1,3,4,9-tetrahydro-1-methylpyrano[3,4-b]indol-1-yl)methyl]-heptanamide, N-[(1,3,4,9-tetrahydro-1-methylpyrano[3,4-b]indol-1-yl)methyl]-cyclopentancarboxamide and N-[(1,3,4,9-tetrahydro-1-methylpyrano[3,4-b]indol-1-yl)methyl]-benzenepropanamide.

EXAMPLE 6

N-[(1,3,4,9-Tetrahydro-1-methylpyrano[3,4-b]indol-1-yl)methyl]-cyclohexancarboxamide (II; R$^1$ and R$^3$=H, R$^2$=cyclohexyl and R$^4$=Me)

A mixture of 1,3,4,9-tetrahydro-1-methylpyrano[3,4-b]indole-1-methanamine(2.6 g, described in Example 3), triethylamine (1.34 g), cyclohexylcarbonyl chloride (1.94 g) and dry tetrahydrofuran (60 ml) is stirred at 25° C. for 18 hours, filtered and evaporated. The residue is crystallized from benzene-hexane to obtain the title compound (3.8 g); mp 174°–175° C.; nmr (CDCl$_3$) δ0.85–2.25(m), 1.55(s), 2.81(m), 3.79(m), 4.00(m), 5.96(t), 6.9–7.2(m) and 9.71(s).

Anal.: Calculated for C$_{20}$H$_{26}$N$_2$O$_2$: C, 73.59; H, 8.03; N, 8.58% Found: C, 73.57; H, 8.04; N, 8.53%

In the same manner but replacing 1,3,4,9-tetrahydro-1-methylpyrano[3,4-b]indole-1-methanamine with an equivalent amount of another compound of formula V described in Example 3, the following compounds for formula II are obtained, respectively: N-[(8-ethyl-1,3,4,9-tetrahydro-1-methylpyrano[3,4-b]indol-1-yl)methyl]-cyclohexancarboxamide, N-[(7-methoxy-1,3,4,9-tetrahydro-1-methylpyrano[3,4-b]indol-1-yl)methyl]-cyclohexancarboxamide, N-[(6-phenyl-1,3,4,9-tetrahydro-1-methylpyrano[3,4-b]indol-1-yl)methyl]-cyclohexancarboxamide, N-[(1-propyl-1,3,4,9-tetrahydropyrano[3,4-b]indol-1-yl)methyl]cyclohexancarboxamide, N-[1-(1-ethyl-1,3,4,9-tetrahydropyrano[3,4-b]indol-1-yl)propyl]cyclohexancarboxamide, N-[(1-ethyl-1,3,4,9-tetrahydropyrano[3,4-b]indol-1-yl)phenylmethyl]-cyclohexancarboxamide, N-[1-(1-butyl-1,3,4,9-tetrahydropyrano[3,4-b]indol-1-yl)-2-phenylethyl]- cyclohexancarboxamide, N-[1-(6-chloro-1,3,4,9-tetrahydro-1-methylpyrano[3,4-b]indol-1-yl)ethyl]-cyclohexancarboxamide, N-[1-(6-nitro-1,3,4,9-tetrahydro-1-methylpyrano[3,4-b]indol-1-yl)ethyl]-cyclohexancarboxamide and N-[1-(5-trifluoromethyl-1,3,4,9-tetrahydro-1-methylpyrano[3,4-b]-indol-1-yl)ethyl]-cyclohexancarboxamide.

EXAMPLE 7

N,N-Dimethyl-N'-[(1,3,4,9-tetrahydro-1-methylpyrano[3,4-b]indol-1-yl)methyl]-urea (II; $R^1$ and $R^3=H$, $R^2=NMe_2$ and $R^4=Me$)

Dimethylcarbamic chloride (3.95 g) is added to a solution at 0° C. of 1,3,4,9-tetrahydro-1-methylpyrano[3,4-b]indole-1-methanamine (7.9 g, described in Example 3), triethylamine (3.7 g) and tetrahydrofuran (200 ml) over a period of 5 minutes. The mixture is stirred at 0° to 5° C. for 30 minutes and at 25° C. for 18 hours. Diethyl ether (200 ml) is added, the mixture is filtered and the filtrate is evaporated. The residue is crystallized from diethyl ether to obtain the title compound (9.0 g); mp 153°-155° C.; ir (CHCl$_3$) 3450-3250 and 1635 cm$^{-1}$; nmr(CDCl$_3$) $\delta$1.51(s) and 2.69(m).

In the same manner but replacing dimethylcarbamic chloride with an equivalent amount of 3-[(N-methyl-N-propyl)amino]propanoyl chloride, 4-(1-piperidinyl)butanoyl chloride or 3-[(N,N-diethyl)-amino]pentanoyl chloride, the following compounds of formula II are obtained, respectively: N-[(1,3,4,9-tetrahydro-1-methylpyrano[3,4-b]indol-1-yl)methyl]-3-[(N-methyl-N-propy)amino]propanamide,N-[(1,3,4,9-tetrahydro-1-methylpyrano[3,4-b]indol-1-yl)methyl]-4-(1-piperidinyl)butanamide and N-[(1,3,4,9-tetrahydro-1-methylpyrano[3,4-b]indol-1-yl)methyl]-3-[(N,N-diethyl)amino]-pentanamide.

EXAMPLE 8

2-Chloro-N-[(1,3,4,9-tetrahydro-1-methylpyrano[3,4-b]indol-1-yl)methyl]-acetamide (VIII; $R^1$ and $R^3=H$, $R^4=Me$ and $R^{20}=CH_2Cl$)

A mixture of 1,3,4,9-tetrahydro-1-methylpyrano[3,4-b]indole-1-methanamine(15 g, described in Example 11), triethylamine(7 g), chloroacetyl chloride (7.9 g) and tetrahydrofuran (300 ml) is stirred at 0° C. for 5 minutes and at 25° C. for 18 hours, filtered and evaporated. The residue is crystallized from chloroform-diethyl ether to obtain the title compound (13.7 g); mp 186°-187° C.; nmr (CDCl$_3$) $\delta$3.41(d), 3.61(d), 3.89(m), 4.09(s), 6.75-7.50(m) and 8.0(t).

Anal. Calculated for C$_{15}$H$_{17}$ClN$_2$O$_2$: C,61.53; H, 5.85; N, 9.56% Found: C,61.52; H, 5.90; N, 9.57%

In the same manner but replacing chloroacetyl chloride with an equivalent amount of 4-chlorobutanoyl chloride or 6-chlorohexanoyl chloride, the following compounds of formula VII are obtained, respectively: 4-chloro-N-[(1,3,4,9-tetrahydro-1-methylpyrano[3,4-b]indol-1-yl)methyl]butanamide and 6-chloro-N-[(1,3,4,9-tetrahydro-1-methylpyrano[3,4-b]indol-1-yl)methyl]-hexanamide.

EXAMPLE 9

1,3a-Dimethyl-3,3a,5,6-tetrahydro-4-oxa-2,10b-diazafluoranthene (VI; $R^1$ and $R^3=H$, and $R^2$ and $R^4=Me$)

A mixture of N-[(1,3,4,9-tetraydro-1-methylpyrano[3,4-b]indol-1-yl)methyl]-acetamide (2.7 g, described in Example 1), phosphorus oxychloride (1.8 ml) and dry benzene (150 ml) is stirred and refluxed for 2 hours, cooled and washed with water (10° C.). The aqueous layer is separated, basified with 5 N sodium hydroxide, and extracted with chloroform. The combined organic extracts are dried over magnesium sulfate, filtered and evaporated to give a residue of the title compound. The residue is dissolved in diethyl ether and hydrogen chloride is added until precipitation is completed. The precipitate is collected and crystallized from ethanol-diethyl ether to obtain the hydrochloride salt of the title compound (1.45 g); mp 226°-227° C.; ir(CHCl$_3$) 2500, 1815, 1623, 1536, 1662 and 1575 cm$^{-1}$; nmr (CDCl$_3$) $\delta$1.66(s), 2.90(m), 3.32(s), 3.48(d), 4.30(m) and 7.51(m).

Anal. Calculated for C$_{15}$H$_{16}$N$_2$O$_2$.HCl: C,65.09; H,6.19; N,10.12; Cl,12.81%. Found: C,64.77; H,6.21; N,10.31; Cl,12.76%.

EXAMPLE 10

3,3a,5,6-Tetrahydro-1,3,3a-trimethyl-4-oxa-2,10b-diazafluoranthene (VI; $R^1=H$, and $R^2$, $R^3$ and $R^4=Me$)

A mixture of N-[1-(1,3,4,9-tetrahydro-1-methylpyrano[3,4-b]indol-1-yl)ethyl]-acetamide (2.0 g, described in Example 2) and phosphorus oxychloride (10 ml) is heated at 100°-110° C. for 3 hours and evaporated. The residue is partioned between chloroform and 10% sodium carbonate. The organic layer is collected, washed with water, saturated brine solution and dried over magnesium sulfate. The residue is chromatographed on silica gel using chloroform. The eluates are evaporated to give a less polar isomer, isomer A(0.40 g), of the title compound, nmr(CDCl$_3$) $\delta$0.86(d) and 3.74(q) and a more polar isomer, isomer B(0.40 g), of the title compound nmr(CDCl$_3$) $\delta$0.78(d) and 4.07(q).

EXAMPLE 11

3,3a,5,6-Tetrahydro-1-cyclohexyl-3a-methyl-4-oxa-2,10b-diazafluoranthene (VI; $R^1$ and $R^3=H$, $R^2=$cyclohexyl and $R^4=Me$)

A mixture of N-[(1,3,4,9-tetrahydro-1-methylpyrano[3,4-b]indol-1-yl)methyl]-cyclohexancarboxamide(1.3 g, described in Example 6) and phosphorus oxychloride (50 ml) is refluxed for 60 minutes and evaporated. The residue is dissolved in chloroform. This solution is washed quickly with 5% sodium hydroxide, dried over magnesium sulfate, filtered and evaporated. The residue is chromatographed on silica gel using chloroform and the eluates are evaporated to give the title compound (0.70 g), nmr(CDCl$_3$) $\delta$0.9-2.6(multiplets), 3.23(d), 3.83(d) and 4.20(m).

EXAMPLE 12

5-(2-Chloroethyl)-1,4-dimethylpyrimido[1,6-a]indole (I; $R^1$ and $R^3=H$, $R^2$ and $R^4=Me$ and $R^5=Cl$)

A mixture of N-[(1,3,4,9-tetrahydro-1-methylpyrano-[3,4-b]indol-1-yl)methyl]-acetamide (15 g, described in Example 1) and phosphorus oxychloride (120 ml) is refluxed for 3 hours. The mixture is evaporated under reduced pressure using an oil bath initially at 100° C. and finally at 140° C. until the volatiles are removed. The solid residue is stirred with chloroform for several hours, and the resulting solution is washed quickly with a cold 10% solution of sodium hydroxide. After evaporation of the solution, the product is crystallized from ethyl acetate to obtain the title compound (10.8 g); mp 124°-125° C., ir (CHCl$_3$) 1609, 1590, 1564 and 1529 cm$^{-1}$; nmr(CDCl$_3$) δ2.56(s), 3.02(s), 3.67(m), and 7.15–8.30(m).

Anal. Calculated for C$_{15}$H$_{15}$ClN$_2$: C,69.62; H,5.84; N,10.83; Cl,13.71% Found: C,69.41; H,5.92; N,10.70; Cl,13.71%

In the same manner but replacing N-[(1,3,4,9-tetrahydro-1-methylpyrano[3,4-b]indol-1-yl)methyl]-acetamide with an equivalent amount of 1,3a-dimethyl-3,3a,5,6-tetrahydro-4-oxa-2,10b-diazafluoranthene (described in Example 9), the title compound is obtained.

Similarly, by replacing N-[(1,3,4,9-tetrahydro-1-methylpyrano[3,4-b]indol-1-yl)methyl]-acetamide with an equivalent amount of the appropriate compound of formula IIa described in Example 1, the following compounds of formula I are obtained, respectively: 9-ethyl-5-(2-chloroethyl)-1,4-dimethylpyrimido[1,6-a]indole,8-methoxy-5-(2-chloroethyl)-1,4-dimethylpyrimido[1,6-a]indole, 7-phenylmethoxy-5-(2-chloroethyl)-1,4-dimethylpyrimido[1,6-a]indole, 4-propyl-5-(2-chloroethyl)-1-methylpyrimido[1,6-a]indole, 5-(2-chloroethyl)-3,4-diethyl-1-methylpyrimido[1,6-a]indole, 5-(2-chloroethyl)-1,4-diethyl-3-phenylpyrimido[1,6-a]indole, and 4-butyl-5-(2-chloroethyl)-1-methyl-3-phenylmethyl-pyrimido[1,6-a]indole.

EXAMPLE 13

5-(2-Bromoethyl)-1,4-dimethylpyrimido[1,6-a]indole (I; R$^1$ and R$^3$=H, R$^2$ and R$^4$=Me and R$^5$=Br)

A mixture of N-[(1,3,4,9-tetrahydro-1-methylpyrano[3,4-b]indol-1-yl)methyl]-acetamide (3.0 g, described in Example 1), and phosphorus tribromide (30 ml) is heated at 110° C. for 60 minutes and then at 160°–170° C. for 2 hours. After cooling, the reaction mixture is evaporated under reduced pressure and the residue is partitioned between 10% sodium bicarbonate and chloroform. The organic phase is separated, dried and evaporated. The residue is chromatographed on neutral alumina using chloroform. The eluates are evaporated and crystallized from methanol-water to obtain the title compound (1.5 g), mp 142°–143° C., nmr(CDCl$_3$) δ2.57(s), 3.05(s), 3.65(m) and 7.15–8.30(m).

Anal. Calculated for C$_{15}$H$_{15}$N$_2$Br: C,59.41; H,4.98; N,9.24% Found: C,59.60; H,5.07; N,9.09%

In a similar manner, a mixture of N-[(1,3,4,9-tetrahydro-1-methylpyrano[3,4-6]indol-1-yl)methyl]-cyclohexancarboxamide (2.0 g, described in Example 6) and phosphorus tribromide (20 ml) is heated at 150° C. for 10 min and evaporated under reduced pressure (2 mm Hg). The residue is partitioned between chloroform and 5% sodium hydroxide. The organic phase is separated, dried over magnesium sulfate and evaporated. The residue is dissolved in benzene and the solution is washed with water, dried and evaporated. The residue is crystallized from diethyl ether-hexane to obtain 5-(2-bromoethyl)-B 1-cyclohexyl-4-methylpyrimido[1,6-a]indole(1.8 g), mp 137°–139° C.;

Anal. Calculated for C$_{20}$H$_{23}$BrN$_2$: C,64.68; H,6.24; N,7.54% Found: C,64.34; H,6.26; N,7.62%

The latter compound of formula I is obtained also in the following manner: Phosphorus tribromide (8.13 g) is added to a solution of N-[(1,3,4,9-tetrahydro-1-methylpyrano[3,4-b]indol-1-yl)methyl]cyclohexancarboxamide(3.01 g, described in Example 6) in chloroform (100 ml). The mixture is refluxed for 60 min, cooled, washed with 5% sodium hydroxide, dried over magnesium sulfate and evaporated. The residue is refluxed with absolute diethyl ether and filtered. The filtrate is diluted with hexane and crystals (2.0 g) of 5-(2-bromoethyl)-1-cyclohexyl-4-methylpyrimido[1,6-a]indol,mp 137°–139° C., are obtained. In the same manner but replacing chloroform with toluene, the latter compound (2.0 g) of formula I,mp 137°–139° C., is obtained.

EXAMPLE 14

5-(2-Chloroethyl)-1,3,4-trimethylpyrimido[1,6-a]indole (I; R$^1$=H, R$^2$, R$^3$ and R$^4$=Me and R$^5$=Cl)

A mixture of N-[(1-(1,3,4,9-tetrahydro-1-methylpyrano[3,4-b]indol-1-yl)ethyl]-acetamide (9.0 g, described in Example 2), phosphorus oxychloride (120 ml) and dry benzene (40 ml) is distilled, a 50 ml fraction being removed. The remaining mixture is refluxed for 3 hours and evaporated under reduced pressure. The residue is heated at 160°–180° C. (for 90 minutes) and cooled. The crude product is dissolved in chloroform and the solution is washed quickly with ice-cold 5% sodium hydroxide. The organic phase is dried over magnesium sulfate and evaporated. The residue is chromatographed on silica gel using chloroform and the eluates are evaporated to give the title compound (3.1 g); mp 91°–92° C.; ir (CHCl$_3$) 1605,1590,1565 and 1525 cm$^{-1}$; nmr (CDCl$_3$) δ2.39(s), 2.50(s), 2.97(s), 3.62(m) and 7.25–8.25(m).

In the same manner but replacing N-[1-(1,3,4,9-tetrahydro-1-methylpyrano[3,4-b]indol-1-yl)ethyl]-acetamide with an equivalent amount of isomer A or isomer B of 3,3a,5,6-tetrahydro-1,3,3a-trimethyl-4-oxa-2,10b-dizafluoranthene (described in Example 10), the title compound is obtained.

In the same manner but replacing N-[1-(1,3,4,9-tetrahydro-1-methylpyrano[3,4-b]indol-1-yl)ethyl]-acetamide with another compound of formula IIa described in Example 2, the following compounds of formula I are obtained, respectively:

7-chloro-5-(2-chloroethyl)-1,3,4-trimethyl-pyrimido[1,6-a]indole, 5-(2-chloroethyl)-1,3,4-trimethyl-7-nitropyrimido[1,6-a]indole and 5-(2-chloroethyl-1,3,4-trimethyl-6-trifluoromethyl-pyrimido[1,6-a]indole.

EXAMPLE 15

5-(2-Chloroethyl)-4-methyl-1-propylpyrimido[1,6-a]indole (I; R$^1$ and R$^3$=H, R$^2$=Pr, R$^4$=Me and R$^5$=Cl)

A solution of N-[(1,3,4,9-tetrahydro-1-methylpyrano[3,4-b]indol-1-yl)methyl]-butanamide (13.0 g, described in Example 5) in benzene (20 ml) is added dropwise to phosphorus oxychloride (200 ml) at 25° C. upon stirring. A fraction of 30 ml is distilled off and the remaining solution is refluxed for 3 hours. Phosphorus oxychloride is removed by vacuum distillation and the residue is heated at 150°–160° C. for 1 hour. The product is partitioned between chloroform and 10% sodium hydroxide and the organic phase is washed with water and evaporated. The resultant oil is crystallized from aqueous methanol to give the title compound (10.0 g). The title compound is recrystallized from hexane, mp 109°–110° C.; nmr(CDCl$_3$) δ1.18(t), 2.03(sextuplet), 2.58(s), 3.33(t), 3.69(m) and 7.2–8.3(m).

Anal: Calculated for C$_{17}$H$_{19}$ClN$_2$:C,71.18; H,6.68; N,9.77%. Found: C,71.12; H,6.76; N,9.84%.

In the same manner but replacing N-[(1,3,4,9-tetrahydro-1-methylpyrano[3,4-b]indol-1-yl)methyl]-butanamide with another compound of Formula II described in Examples 4,5 and 6, the following compounds of formula I are obtained, respectively:

- 5-(2-chloroethyl)-4-methylpyrimido[1,6-a]indole;
- 5-(2-chloroethyl)-4-methyl-1-(2-methylpropyl)-pyrimido[1,6-a]indole;
- 5-(2-chloroethyl)-1-hexyl-4-methylpyrimido[1,6-a]indole;
- 5-(2-chloroethyl)-1-cyclopentyl-4-methyl-pyrimido[1,6-a]indole;
- 5-(2-chloroethyl)-4-methyl-1-(2-phenylethyl)-pyrimido[1,6-a]indole;
- 5-(2-chloroethyl)-1-cyclohexyl-4-methyl-pyrimido[1,6-a]indole, mp 144°–145°; ir(CHCl$_3$)1620, 1600 and 1530 cm$^{-1}$; nmr(CDCl$_3$) $\delta$1.0–2.45(m), 2.59(s), 3.35(m), 3.68(m) and 7.1–8.1(m);
- 5-(2-chloroethyl)-1-cyclohexyl-9-ethyl-1-methyl-pyrimido[1,6-a]indole;
- 5-(2-chloroethyl)-B 1-cyclohexyl-8-methoxy-1-methylpyrimido[1,6-a]indole;
- 5-(2-chloroethyl)-1-cyclohexyl-1-methyl-7-phenyl-methylpyrimido[1,6-a]indole;
- 5-(2-chloroethyl)-1-cyclohexyl-4-propyl-pyrimido[1,6-a]indole;
- 5-(2-chloroethyl)-1-cyclohexyl-3,4-diethyl-pyrimido[1,6-a]indole;
- 5-(2-chloroethyl)-1-cyclohexyl-4-ethyl-3-phenyl-pyrimido[1,6-a]indole;
- 4-butyl-5-(2-chloroethyl)-1-cyclohexyl-3-phenylme-thylpyrimido[1,6-a]indole;
- 7-chloro-5-(2-chloroethyl)-1-cyclohexyl-3,4-dime-thylpyrimido[1,6-a]indole;
- 5-(2-chloroethyl)-1-cyclohexyl-3,4-dimethyl-7-nitropyrimido[1,6-a]indole and 5-(2-chloroethyl)-1-cyclohexyl-3,4-dimethyl-6-trifluoromethyl-pyrimido[1,6-a]indole.

EXAMPLE 16

5-(2-Chloroethyl)-1-(N,N-dimethylamino)-4-methyl-pyrimido[1,6-a]indole (I; R$^1$ and R$^3$=H, R$^2$=NMe$_2$, R$^4$=Me and R$^5$=Cl)

A mixture of N,N-dimethyl-N'-[(1,3,4,9-tetrahydro-1-methylpyrano[3,4-b]indol-1-yl)methyl]-urea (2.0 g, described in Example 7) and phosphorus oxychloride (50 ml) is refluxed for 90 minutes. Under reduced pressure, the volatiles are evaporated and the residual viscous material is heated at 160° C. for 60 minutes. After cooling, the crude product is dissolved in chloroform and washed quickly with ice-cold 5% sodium hydroxide. The organic phase is dried over magnesium sulfate, filtered and evaporated. The residue is chromatographed on silica gel using chloroform. The eluates are evaporated to give the title compound (0.60 g), nmr(CDCl$_3$) $\delta$2.41(d), 2.77(s), 3.55(m), 6.88(m) and 7.0–8.15(m).

The title compound is dissolved in diethyl ether and hydrogen chloride is added until precipitation is complete. The precipitate is collected and crystallized from acetonitrile-diethyl ether to obtain the hydrochloride salt of the title compound, mp 203°–204° C., ir(nujol) 2540 and 1640 cm$^{-1}$ and uv(MeOH) $\lambda_{max}$ 244($\epsilon$32,360), 305($\epsilon$10,280) and 318($\epsilon$11,000) nm.

Anal. Calculated for C$_{16}$H$_{18}$ClN$_3$·HCl: C,59.26; H,5.90; N,12.96% Found: C,59.18; H,5.85; N,13.07%

In the same manner but replacing N,N-dimethyl-N'-[(1,3,4,9-tetrahydro-1-methylpyrano[3,4-b]indol-1-yl)methyl]-urea with an equivalent amount of another compound of formula II are described in Example 7, the following compounds of formula I are obtained, respectively:

- 5-(2-chloroethyl)-1-[2-(N-methyl-N-propylamino)ethyl]-4-methylpyrimido[1,6-a]indole,
- 5-(2-chloroethyl)-1-[3-(1-piperidinyl)propyl]-4-methylpyrimido[1,6-a]indole and 5-(2-chloroethyl)-1-[4-(N,N-diethylamino)butyl]-4-methylpyrimido[1,6-a]indole.

EXAMPLE 17

5-(2-Chloroethyl)-1-(chloromethyl)-4-methyl-pyrimido[1,6a]indole (IX; R$^1$ and R$^3$=H, R$^4$=Me, R$^5$=Cl and R$^{20}$=CH$_2$Cl)

A mixture of 2-chloro-N-[(1,3,4,9-tetrahydro-1-methylpyrano[3,4-b]indol-1-yl)methyl]-acetamide (9.0 g, described in Example 8) and phosphorus oxychloride (200 ml) is refluxed for 60 minutes and evaporated slowly to dryness under reduced pressure (10 mm Hg, the final bath temperature 140° C.). The residue is dissolved in chloroform and the solution is washed quickly with ice-cold 5% solution of sodium hydroxide, dried over magnesium sulfate, filtered and evaporated. The residue is chromatographed through a column of silica gel (300 g) using chloroform. The eluates are evaporated and the residue is crystallized from ethyl acetate to obtain the title compound (5.5 g); mp 160°–161° C., nmr(CDCl$_3$) $\delta$2.53(s), 3.62(m), 4.94(s) and 7.10–8.20(m).

Anal. Calculted for C$_{15}$H$_{14}$Cl$_2$N$_2$: C,61.44; H,4.81; N,9.55% Found: C,61.47; H,4.70; N,9.37%

In the manner but replacing 2-chloro-N-[(1,3,4,9-tetrahydro-1-methylpyrano[3,4-b]indol-1-yl)methyl]-acetamide with an equivalent amount of another compound of formula VII described in Example 8, the following compounds of formula IX are obtained, respectively: 5-(2-chloroethyl)-1-(3-chloropropyl)-4-methyl-pyrimido[1,6-a]indole and 5-(2-chloroethyl)-1-(5-chloropentyl)-4-methylpyrimido[1,6-a]indole.

EXAMPLE 18

1,3,4-Trimethylpyrimido[1,6-a]indole-5-ethanol (I;R$^1$=H; R$^2$, R$^3$ and R$^4$=Me and R$^5$=OH)

A mixture of N-[1-(1,3,4,9-tetrahydro-1-methyl-pyrano[3,4-b]indol-1-yl)ethyl]-acetamide (6.0 g, described in Example 2) and phosphorus oxychloride (80 ml) is refluxed for 3 hours. The volatiles are removed under reduced pressure and the residue is heated at 160° C. under vacuum (6 mm Hg) for 2 hours. After cooling, the dark material is partitioned between 10% sodium hydroxide and chloroform. The resultant emulsion is kept several hours until the phases are separated. The organic layer is dried over sodium sulfate, filtered and evaporated. The crude product (3.7 g) is chromatographed on neutral alumina using benzene as eluent. The eluate is evaporated and the residue is crystallized from ethyl acetate to give the title compound (0.6 g); mp 187°–188° C., ir (nujol) 3270 cm$^{-1}$, uv (MeOH) $\lambda_{max}$ 252,303,316 and 327 nm; $\epsilon$=41200, 6850, 12180 and 14620 respectively, nmr (DMSO-d$_6$) $\delta$2.29(s), 2.48(s), 2.91(s) and 7.15–8.25(m).

Anal. Calculated for C$_{16}$H$_{18}$N$_2$O: C,75.56; H,7.13; N,11.02%. Found: C,75.37; H,7.26; H,11.28%.

EXAMPLE 19

1,4-Dimethyl-5-[2-(methoxy)ethyl]pyrimido[1,6-a]indole (I; $R^1$ and $R^3$=H, $R^2$ and $R^4$=Me and $R^5$=OMe)

A mixture of 5-(2-chloroethyl)-1,4-dimethylpyrimido[1,6-a]indole(7.5 g, described in Example 12) and sodium (0.7 g) in methanol (200 ml) is refluxed for 12 hours. Methanol is removed in vacuo and the residue is partitioned between water and chloroform. The organic phase is dried over magnesium sulfate, filtered and concentrated to 20 ml. This solution is acidified with hydrogen chloride in diethyl ether and diethyl ether is added until precipitation is complete. The precipitate (5.5 g) is crystallized from acetonitrile to give the hydrochloride salt of the title compound; mp 242° C.; ir (nujol) 2490 and 1647 cm$^1$; uv(MeOH) $\lambda_{max}$ 251, 306 and 320 nm, $\epsilon$=40100, 8400 and 9700 respectively; nmr (DMSOd$_6$ with the addition of D$_2$O): δ2.59(s), 3.20(s), 3.26(s) and 3.2–3.7(m).

Anal. Calculted for $C_{16}H_{18}N_2O.HCl$: C,66.09; H,6.59; N,9.64% Found: C,66.17; H,6.58; N,9.76%

In the same manner but replacing methanol with an equivalent amount of ethanol, propanol or 2-methylpropanol, the following compounds of formula I are obtained, respectively: 5-[2-(ethoxy)ethyl]-1,4-dimethylpyrimido[1,6-a]indole, 1,4-dimethyl-5-[2-(propoxy)ethyl]pyrimido[1,6-a]indole and 1,4-dimethyl-5-[2-(2-methylpropoxy)ethyl]pyrimido[1,6-a]indole.

EXAMPLE 20

1-Pyrrolidinecarbodithioic acid, β-(1,4-dimethylpyrimido[1,6-a]indol-5-yl)ethyl ester (I; $R^1$ and $R^3$=H, $R^2$ and $R^4$=Me and $R^5$=1-pyrrolidinylthioxomethylthio)

To a stirred solution of sodium hydroxide (12 g) in water (52 ml) is added pyrrolidine (21.3 g) followed by carbondisulfide (24 g). The exothermic reaction sets in, and the mixture is cooled to 0°–5° C. for 1 hour. Stirring is continued for an additional hour at room temperature and the precipitate is filtered, crystallized from methanol-diethyl ether (mp<250° C.) and air-dried. Sodium 1-pyrrolidinedithionate thus obtained is used in the next step. An aqueous solution of this sodium salt (4.4 g) is added to a solution of 5-(2-chloroethyl)-1,4-dimethyl-, pyrimido[1,6-a]indole (6 g, described in Example 12) in ethanol (200 ml), and the mixture is refluxed for 15 hours. The resultant slurry is evaporated and the residue is taken up between chloroform and water. The organic phase is dried over magnesium sulfate and evaporated and the residue is crystallized from ethyl acetate-hexane to obtain the title compound (6.1 g); mp 143°–144° C., nmr (CDCl$_3$) δ1.98(m), 2.49(s), 2.93(s), 3,47(m), 3.85(t), and 6.9–8.1(m); ir (CHCl$_3$) 1612,1597,1568 and 1532 cm$^{-1}$; and uv (MeOH) $\lambda_{max}$ 251,273,298,312, and 326 nm; $\epsilon$=49500,19175, 6500,9400 and 12635, respectively.

Anal. Calculated for $C_{20}H_{23}N_3S_2$: C,64.98; H,6.28; N,11.37% Found: C,65.14; H,6.22; N,11.24%

EXAMPLE 21

5-[2-[(4,5-dihydro-1H-imidazol-2-yl)thio]ethyl]-1,4-dimethylpyrimido[1,6-a]indole

[I; $R^1$ and $R^3$=H, $R^2$ and $R^4$=Me and $R^5$=(4,5-dihydro-1H-imidazol-2-yl)thio]

A mixture of 2-imidazolidinethione (3.1 g), 5-(2-bromoethyl)-1,4-dimethylpyrimido[1,6-a]indole (6 g, described in Example 13) and dry dioxane (400 ml) is refluxed for 6 hours. The resulting precipitate is collected by filtration and dissolved in water and the solution is neutralized with aqueous sodium bicarbonate. After adding a few drops of 10% sodium hydroxide, the aqueous mixture is extracted with chloroform. The combined extracts are washed with water, dried over magnesium sulfate, filtered and evaporated. The residue is crystallized from acetonitrile to obtain the title compound (3.8 g): mp 157°–159° C.; ir (CHCl$_3$) 3400, 1610, 1595 and 1570 cm$^{-1}$; uv(MeOH) $\lambda_{max}$ 250,299,311 and 325 nm; $\epsilon$=35200, 4840, 8200, and 10870, respectively; and nmr (CDCl$_3$) δ2.52(s), 2.99(s), 3.43(m), 3.60(s), 4.25(s) and 7.1–8.2(m).

Anal. Calculated for $C_{18}H_{20}N_4S$: C,66.63; H,6.22; N,17.26% Found: C,66.43; H,6.17; N,16.96%

The title compound (3.9 g) is dissolved in acetonitrile, acidified with a solution of hydrogen chloride in diethyl ether and the resultant precipitate is collected and crystallized from acetonitrile, mp 222°–225° C. Further crystallization from ethanol-diethyl ether furnished 3.5 g of the hydrochloride salt of the title compound: mp 259°–262° C.; ir(nujol) 3420,2650, and 1650 cm$^{-1}$; and uv(MeOH) $\lambda_{max}$ 250,280,299,309 and 323 nm; $\epsilon$=35300,8260,8100 and 9420, respectively.

EXAMPLE 22

1,4,N,N-Tetramethylpyrimido[1,6-a]indole-5-ethanamine (I; $R^1$ and $R^3$=H, $R^2$ and $R^4$=Me and $R^5$=N(Me)$_2$)

A mixture of 5-(2-chloroethyl)-1,4-dimethylpyrimido[1,6-a]indole (6 g, described in Example 12), dimethylamine (40% aqueous, 150 ml), and dioxane (150 ml) is refluxed for 1 hour and evaporated under reduced pressure. The residue is partitioned between chloroform and 1% aqueous sodium hydroxide and the organic phase is dried over magnesium sulfate, filtered and evaporated to give a residue of the title compound (4.5 g), nmr (CDCl$_3$) δ2.39(s), 2.58(s), 3.05(s) and 7.10–8.35(m).

The title compound is dissolved in chloroform, the solution is acidified with a solution of hydrogen chloride in diethyl ether and the precipitate is collected and crystallized from methanol-diethyl ether to obtain the title compound as the dihydrochloride salt; mp 279°–281° C.; uv(MeOH) $\lambda_{max}$ 256,279,297,308, and 322 nm; $\epsilon$=31500,8600, 6000,8600 and 9600, respectively.

Anal. Calculated for $C_{17}H_{21}N_3.2HCl$: C,60.00; H,6.81; N,12.34% Found: C,59.84; H,6.96; N,12.53%

In the same manner but replacing dimethylamine with an equivalent amount of diethylamine, N-methyl-N-(1-methylethyl)amine, N-methyl-N-butylamine or N-ethyl-N-hexylamine and refluxing the solution for 4 to 10 hours, the following compounds of formula I are obtained, respectively: N,N-diethyl-1,4-dimethylpyrimido[1,6-a]indole-5-ethanamine; nmr(CDCl$_3$) δ1.06(t), 2.45(s), 2.89(s), 6.90(m) and 7.0–8.0(m), and the dihydrochloride salt of the latter compound, mp 259°–260° C., ir (nujol)2520 and 2400 cm$^{-1}$ and uv(MeOH) $\lambda_{max}$ 281,308, and 322 nm, $\epsilon$=8550,8750, and 9870. respectively;

N-(1-methylethyl)-1,4-N-trimethylpyrimido[1,6-a]indole-5-ethanamine, nmr (CDCl$_3$) δ1.05(d), 2.41(s), 2.56(s), 3.02(s) and 7.1–8.3(m), and the dihydrochloride salt of the latter compound, mp 250°–251° C., uv(MeOH) $\lambda_{max}$ 284,298,308 and 322 nm, $\epsilon$=8540,6030, 8800 and 9800, respectively; N-butyl-1,4,N-trimethylpyrimido[1,6-a]indole-5-ethanamine and N-ethyl-N-hexyl-1,4-dimethylpyrimido[1,6-a]indole-5-ethanamine.

Similarily, by replacing 5-(2-chloroethyl)-1,4-dimethylpyrimido[1,6-a]indole with an equivalent amount of another compound of formula I described in Example 12 and using N-methyl-N-(1-methylethyl)amine, the following compounds of formula I are obtained, respectively; 9-ethyl-1,4,N-trimethyl-N-(1-methylethyl)-pyrimido[1,6-a]indole-5-ethanamine, 8-methoxy-1,-4,N-trimethyl-N-(1-methylethyl)pyrimido[1,6-a]indole-5-ethanamine,7-phenylmethoxy-1,4,N-trimethyl-N-(1-methylethyl)pyrimido[1,6-a]indole-5-ethanamine,1,N-dimethyl-N-(1-methylethyl)-4-propylpyrimido[1,6-a]indole-5-ethanamine,3,4-diethyl-1,N-dimethyl-N-(1-methylethyl)pyrimido[1,6-a]indole-5-ethanamine,1,4-diethyl-N-methyl-N-(1-methylethyl)-3-phenyl-pyrimido[1,6-a]indole-5-ethanamine, and 4-butyl-1, N-dimethyl-N-(1-methylethyl)-3-phenylpyrimido[1,6-a]indole-5-ethanamine.

EXAMPLE 23

N-(2-Propynyl)-N,1,4-trimethylpyrimido[1,6-a]indole-5-ethanamine (I; $R^1$ and $R^3$=H, $R^2$ and $R^4$=Me and $R^5$=N(Me)CH$_2$C≡CH)

A mixture of 5-(2-chloroethyl)-1,4-dimethylpyrimido[1,6-a]indole (7.75 g, described in Example 12) in water (100 ml) and N-methyl-N-(2-propynyl)amine (5 g) in tetrahydrofuran (200 ml) is stirred and heated at reflux until it becomes homogeneous (cca 1 hr). After further stirring at reflux for 12 hours the solvents are evaporated and the residue is partitioned between chloroform and 10% aqueous sodium carbonate. The organic layer is washed with water, saturated brine, dried over magnesium sulfate, filtered and evaporated. The syrupy residue is chromatographed on neutral alumina and elution with benzene to benzene-chloroform (1:1) afforded 4 g of the title compound; mp 101°–102° C. when crystallized from diethyl ether and nmr (CDCl$_3$) δ2.27(t), 2.43(s), 2.53(s), 2.98(s), 3.48(d), 7.17(s), and 7.25–8.5(m).

The title compound is dissolved in chloroform and the solution is acidified with a solution of hydrogen chloride in diethyl ether. The solution is evaporated and the residue is crystallized from methanol-diethyl ether to obtain the title compound as the dihydrochloride salt: mp 249°–250° C.; ir(nujol) 3400, 3240(water) and 2500(NH+) cm$^{-1}$; uv (MeOH) $\lambda_{max}$ 256,297,307, and 321 nm; ε=32000, 6000, 8600 and 9730, respectively.

In the same manner but replacing N-methyl-N-(2-propynyl)amine with an equivalent amount of N-cyclobutylmethyl-N-methylamine, N-ethyl-N-(2-butenyl)amine, N-(3-butynyl)-N-(2-propenyl)amine, N-(3-cyclohexylpropyl)-N-(3-butenyl)amine, N-(2-ethylpropyl)-N-(4-pentynyl)amine or N-(3-methyl-2-butenyl)-N-(2-methylpropyl)amine, the following compounds of formula I are obtained, respectively: N-cyclobutylmethyl-1,4,N-trimethylpyrimido[1,6-a]indole-5-ethanamine, N-(2-butenyl)-N-ethyl-1,4-dimethylpyrimido[1,6-a]indole-5-ethanamine, N-(3-butynyl)-N-(2-propenyl)-1,4-dimethylpyrimido[1,6-a]indole-5-ethanamine, N-(3-cyclohexylpropyl)-N-(3butenyl)-1,4-dimethylpyrimido[1,6-a]indole-5-ethanmine, N-(2-ethylpropyl)-N-(4-pentynyl)-1,4-dimethylpyrimido[1,6-a]indole-5-ethanamine, and N-(3-methyl-2-butenyl)-N-(2-methylpropyl)-1,4-dimethylpyrimido[1,6-a]indole-5-ethanamine.

EXAMPLE 24

1,4,N-Trimethyl-N-(hydroxyethyl)pyrimido[1,6-a]indole-5-ethanamine (I; $R^1$ and $R^3$=H, $R^2$ and $R^4$=Me and $R^5$=N(Me)CH$_2$CH$_2$OH)

A mixture of 5-(2-chloroethyl)-1,4-dimethylpyrimido[1,6-a]indole hydrochloride (5.0 g, described in Example 12) and 20 ml of methylaminoethanol is heated at 130° C. for 5 hours. An excess of the amine is removed under reduced pressure and the residual oil is partitioned between water and chloroform. The organic phase is dried over magnesium sulfate, filtered and evaporated to give the title compound; nmr (CDCl$_3$) δ2.48(s), 2.53(s), 3.00(s), 2.6–3.5(m), 3.31(s), 3.63(t) and 7.05–8.25(m).

The title compound is dissolved in chloroform and the solution is acidified with a solution of hydrogen chloride in diethyl ether and evaporated. The residue is crystallized from methanol-diethyl ether to give the title compound as the dihydrochloride salt (5.0 g): mp 251°–254° C.; ir (nujol) 3200 and 2420 cm$^{-1}$; uv (MeOH) $\lambda_{max}$ 250,256,309, and 323 nm; ε=38060, 32050, 9075, and 11530, respectively.

Anal. Calculated for C$_{18}$H$_{23}$N$_3$O.HCl: C,58.31; H,6.74; N,11.33% Found: C,57.94; H,6.73; N,11.16%

EXAMPLE 25

1,4-Dimethyl-5-[2-(1-pyrrolidinyl)ethyl]pyrimido[1,6-a]indole (I; $R^1$ and $R^3$=H, $R^2$ and $R^4$=Me and $R^5$=1-pyrrolidinyl)

A mixture of 5-(2-chloroethyl)-1,4-dimethylpyrimido[1,6-a]indole(5.0 g, described in Example 12) and pyrrolidine (30 ml) is heated at reflux for 5 hours. An excess of pyrrolidine is removed under reduced pressure and the residue is stripped twice with 50 ml of benzene and then partitioned between water and benzene. The organic layer is separated and extracted with 5% hydrochloric acid. The aqueous part is rendered basic with 20% sodium hydroxide and extracted with chloroform. The combined organic extracts are dried over magnesium sulfate, filtered, and evaporated to give 4.6 g of the title compound which solidified upon standing, mp 96°–97° C. The latter compound is chromatographed on a dry column of neutral alumina (500 g containing 4% of water) using chloroform. The eluates are evaporated to give the title compound (4.2 g); mp 96°–98° C. and nmr (CDCl$_3$) δ1.87(m), 2.58(s), 3.02(s) and 7.1–8.3(m).

The title compound is converted, in the same manner as described in Example 24, to the dihydrochloride salt of the title compound which is crystallized from ethanol-diethyl ether: mp 262°–264° C.; ir (nujol) 2580 cm$^{-1}$; uv (MeOH) $\lambda_{max}$ 250,255,280,298,308 and 323 nm; ε=36060,30100, 7400, 5450, 8500, and 10050, respectively.

Anal. Calculated for C$_{19}$H$_{23}$N$_3$.2HCl: C,62.28; H,6.88; N,11.47%; Found: C,61.98; H,6.61; N,11.31%

In the same manner but replacing pyrrolidine with an equivalent amount of piperidine, hexahydro-1H-azepine, 1,2,5,6-tetrahydropyridine, morpholine or 2,6-dimethylmorpholine and heating the mixture for 5 to 15 hours, the following compounds of formula I are obtained, respectively: 1,4-dimethyl-5-[2-(1-piperidinyl)ethyl]pyrimido[1,6-a]indole dihydrochloride, mp 257°–259° C., ir(nujol) 2660 cm$^{-1}$; uv (MeOH) $\lambda_{max}$ 250, 256, 280, 297, 308 and 323 nm, ε=35630, 30600, 7900, 5540, 8150 and 9400, respectively; 1,4-dimethyl-5-

[2-(hexahydro-1H-azepin-1-yl)ethyl]pyrimido[1,6-a]indole, nmr (CDCl$_3$) δ2.57(s) and 3.03(s) and the dihydrochloride salt, mp 272°-274° C., ir (nujol) 2600 and 2780 cm$^{-1}$; uv (MeOH) λ$_{max}$ 298, 309 and 323 nm, ε=5775, 9000 and 11400, respectively; 1,4-dimethyl-5-[2-(1,2,5,6-tetrahydropyridin-1-yl)ethyl]pyrimido[1,6-a]indole, nmr (CDCl$_3$) δ5.8(m) and dihydrochloride salt, mp 258°-259° C., ir (nujol) 2700 and 2510 cm$^{-1}$; uv (MeOH) λ$_{max}$ 299, 308 and 323 nm, ε=5790, 8400 and 9800, respectively; 1,4-dimethyl-5-[2-(4-morpholinyl)ethyl]pyrimido[1,6-a]indole, nmr (CDCl$_3$) δ2.55(s), 2.63(m), 3.01(s), 3.35(m), 3.80(m) and 7.1-8.3(m) and dihydrochloride salt, mp 250°-252° C., ir (nujol) 2670 and 2360 cm$^{-1}$, uv(MeOH) λ$_{max}$ 250,256,281, 296, 307 and 326 nm, ε=38580, 32820, 8690, 5990, 8580 and 9675 respectively; and 1,4-dimethyl-5-[2-(2,6-dimethyl-4-morpholinyl)ethyl]pyrimido[1,6-a]indole, nmr (CDCl$_3$) δ1.20(d), 2.55(s), 3.03(s) and 7.10-8.30(m) and dimaleate salt, mp 175°-176° C., ir (nujol) 3500, 2350 and 1700 cm$^{-1}$, uv (MeOH) λ$_{max}$ 250, 256, 310 and 324 nm, ε=39230, 33045, 8920 and 12170, respectively.

EXAMPLE 26

1,4-Dimethyl-5-[2-(4-benzoylamino-1-piperidinyl)ethyl]pyrimido[1,6-a]indole (I; R$^1$ and R$^3$=H, R$^2$ and R$^4$=Me and R$^5$=4-benzoylamino-1-piperidinyl)

An intimate mixture of powdered 4-benzoylaminopiperidine (4.08 g) and 5-(2-chloroethyl)-1,4-dimethylpyrimido[1,6-a]indole (5.18 g. described in Example 12) is heated at 150°-160° C. for 30 minutes. After cooling, the melt is dissolved in chloroform, washed with 10% sodium hydroxide and repeatedly with water. The organic phase is dried over magnesium sulfate and evaporated. The residue is chromatographed on silica gel using chloroform-methanol (35:1). The eluates are evaporated and the residue is crystallized from ethanol-diethyl ether to give 4.15 g of the title compound, mp 233°-234° C. The title compound is coverted to the dihydrochloride salt and crystallized from methanol; mp 247° C.; ir (nujol) 3255, 2450 and 1625 cm$^{-1}$; uv(MeOH) λ$_{max}$ 256, 297, 309 and 322 nm; ε=33700, 6000, 9050 and 10880, respectively.

Anal. Calculated For C$_{27}$H$_{30}$N$_4$O.2HCl: C,64.92; H,6.45; N,11.21%. Found: C,64.33; H,6.64; N,10.92%.

EXAMPLE 27

1,4-Dimethyl-5-[2-[4-(4-methoxy)phenyl-1-piperazinyl]ethyl]pyrimido[1,6-a]indole (I; R$^1$ and R$^3$=H, R$^3$ and R$^4$=Me and R$^5$=(4-methoxy)phenyl-1-piperazinyl)

An intimate mixture of 1-(4-methoxyphenyl)piperazine (2.88 g) and 5-(2-chloroethyl)-1,4-dimethylpyrimido[1,6-a]indole (3.88 g, described in Example 12) is heated at 150° C. for 50 minutes. During the reaction time, melting and resolidification of the material is observed. After cooling, the crude product is dissolved in chloroform and the solution is washed with 5% sodium hydroxide. The organic phase is dried and evaporated. The residue is chromatographed on neutral alumina using benzene and changing to chloroform. The eluates are evaporated and the residue (2.4 g) is crystallized from benzene-hexane to give the title compound: mp 137°-138° C.; nmr (CDCl$_3$) δ2.58(s), 3.02(s) and 3.75(s).

The title compound is dissolved in chloroform, the solution is acidified with hydrogen chloride in diethyl ether and the resultant solution is evaporated. The residue is crystallized from methanoldiethyl ether to obtain the title compound as the dihydrochloride salt: mp 278°-279° C.; ir (nujol) 2350 cm$^{-1}$; uv(MeOH) λ$_{max}$ 281,296,306 and 319 nm; ε=9230, 7100, 9000 and 9050, respectively.

Anal. Calculated for C$_{26}$H$_{30}$N$_4$O.2HCl: C,64.05; H,6.61; N,11.49%. Found: C,63.86; H,6.89; N,11.32%.

EXAMPLE 28

1,4-Dimethyl-5-[2-(4-methyl-1-piperazinyl)ethyl]-pyrimido[1,6-a]indole (I; R$^1$ and R$^3$=H, R$^2$ and R$^4$=Me and R$^5$=4-methyl-1-piperazinyl)

5-(2-Chloroethyl)-1,4-dimethylpyrimido[1,6-a]indole hydrochloride (6.0 g, described in Example 12) is suspended in diluted sodium hydroxide, the corresponding base is extracted with chloroform and the solution is evaporated. N-Methylpiperazine (25 ml) is added and the mixture is heated at 130° C. for 5 hours. After cooling, the dark residue is stripped twice with 100 ml portions of benzene, dissolved in 10% hydrochloride acid, and washed with a mixture of ethyl acetate-benzene (1:1). The aqueous phase is rendered basic with sodium hydroxide, extracted with chloroform, and the combined organic extracts are dried and evaporated. The resultant oil is chromatographed on neutral alumina with chloroform and the eluates are acidified with hydrogen chloride in diethyl ether. The solution is evaporated and the residue is crystallized from methanol-diethyl ether to obtain the title compound as the trihydrochloride dihydrate salt (5.1 g) mp 255° C.; ir (nujol): 3380, 2400, and 1645 cm$^{-1}$; uv (MeOH); λ$_{max}$ 250,255,281,295,305 and 319 nm; ε=33330, 29540, 8330, 6030, 8820 and 10180, respectively; nmr (trifluoroacetic acid) δ2.83(s), 3.30(s), 3.57(s), 4.02(m), 4.25(m), 7.25(m), 7.4-8.4(m) and 10.95(s).

Anal. Calculated for C$_{20}$H$_{26}$N$_4$.3HCl.2H$_2$O: C,51.33; H,7.10; N,11.97%. Found: C,51.57; H,6.94; N,12.37%.

EXAMPLE 29

1,4-Dimethyl-5-[2-(1H-imidazol-1-yl)ethyl]-pyrimido[1,6-a]indole (I: R$^1$ and R$^3$=H, R$^2$ and R$^4$=Me and R$^5$=1H-imidazol-1-yl)

A mixture of imidazole (6.9 g), 5-(2-bromoethyl)-1,4-dimethylpyrimido[1,6-a]indole (6.1 g, described in Example 13), and dry dimethylformamide (50 ml) is refluxed for 24 hours. The bromoethyl component can be replaced by the corresponding chloroethyl derivative (5.2 g, described in Example 12). After cooling, the reaction mixture is poured onto ice-water and the aqueous solution is extracted thrice with 100 ml of chloroform. The combined extracts are washed with water to neutrality, dried over magnesium sulfate, filtered and evaporated. The residue is crystallized from acetonitrile to obtain the title compound (4.2 g): mp 165°-167° C.; and nmr (DMSO-d$_6$) δ2.33(s), 2.98(s), 3.50(t), 4.28(t) and 6.80-8.35(m).

Anal. Calculated for C$_{18}$H$_{18}$N$_4$: C,74.45; H,6.25; N,19.30%. Found: C,74.22; H,6.21; N,19.68%.

The title compound (4.2 g) is dissolved in ethanol and acidified with a solution of hydrogen chloride in diethyl ether. The precipitate is collected and crystalized from ethanol to obtain the title compound as the dihydrochloride salt (3.9 g): mp 255°-260° C. (capillary); ir (nujol) 3420, 2600 and 1652 cm$^{-1}$; uv (MeOH) λ$_{max}$ 250,280,299,309 and 322 nm; ε=35300, 8600, 5600, 8610 and 9665, respectively.

EXAMPLE 30

5-[2-(1-Pyrrolidinyl)ethyl]-1,3,4-trimethylpyrimido[1,6-a]indole (I; $R^1$=H; $R^2$, $R^3$ and $R^4$=Me, and $R^5$=1-pyrrolidinyl)

A mixture of 5-(2-chloroethyl)-1,3,4-trimethylpyrimido[1,6-a]indole (3.1 g, described in Example 14) and pyrrolidine (30 ml) is refluxed for 20 hours and evaporated. The residue is stripped with 50 ml of benzene and partitoned between 5% hydrochloric acid and benzene. The aqueous layer is rendered basic with 10% sodium hydroxide and extracted with chloroform. The combined extracts are dried over magnesium sulfate, filtered, concentrated and applied on a column of neutral alumina. Elution with chloroform gave 1.7 g of the title compound; nmr (CDCl$_3$) δ1.86(m), 2.39(s), 2.53(s), 2.72(m), 2.99(s), 3.44(m) and 7.2-8.2(m).

The title compound is dissolved in chloroform and the solution is acidified with a solution of hydrogen chloride in diethyl ether. The solution is evaporated and the solid residue is crystallized from ethanoldiethyl ether to give the monohydrochloride salt of the title compound; mp 263°-264° C.; ir (nujol) 3450, and 3340 (traces of H$_2$O), and 2580 cm$^{-1}$; uv (MeOH) $\lambda_{max}$ 252,256,282,301,311 and 324 nm; ϵ=31200, 29500, 7600, 6705, 10110 and 10800, respectively.

Anal. Calculated for C$_{20}$H$_{25}$N$_3$.HCl: C,69.84; H,7.62; N,12.22%. Found: C,69.07; H,7.54; N,12.15%.

EXAMPLE 31

1-Cyclohexyl-4-methyl-5-[2-(1-pyrrolidinyl)ethyl]-pyrimido[1,6-a]indole (I; $R^1$ and $R^3$=H, $R^2$=cyclohexyl, $R^4$=Me and $R^5$=1-pyrrolidinyl)

A mixture of 5-(2-chloroethyl)-1-cyclohexyl-4-methylpyrimido[1,6-a]indole (3.5 g, described in Example 15) and pyrrolidine (80 ml) is refluxed for 10 hours. The reaction mixture is evaporated, and the residue is chromatographed on a dry column of neutral alumina using chloroform. A major, homogeneous fraction (2.5 g) is crystallized from benzene-hexane to give the title compound; mp 127°-127.5° C.; mass spectrum (rel. intensity) m/e 361(21), 291(4), 277(100), 221(5), 195(7), 167(8) and 94(20).

In the same manner, but replacing 5-(2-chloroethyl)-1-cyclohexyl-4-methylpyrimido[1,6-a]indole with an equivalent amount of 5-(2-bromoethyl)-1-cyclohexyl-4-methylpyrimido[1,6-a]indole (described in Example 13), the title compound is obtained.

The title compound (558 mg) is suspended in methanol (7 ml) and 1.62 N hydrogen chloride in methanol (0.95 ml) is added. The mixture is heated in a sealed vessel until a clear solution is obtained. Diisopropyl ether (50 ml) is added and the monohydrochloride salt of the title compound (520 mg) is collected; mp 289°-290° C. (sealed and evacuated capillary); ir (nujol) 2660, 2560, and 2470 cm$^{-1}$; uv (0.1 N HCl in MeOH) $\lambda_{max}$ 264,293,306, and 319 nm, ϵ=41820, 7200, 10100 and 11195, respectively.

Anal. Calculated for C$_{24}$H$_{31}$N$_3$.HCl: C,72.42; H,8.10; N,10.55; Cl,8.91%. Found: C,72.47; H,8.00; N,10.62; Cl,9.20%.

The title compound is dissolved in chloroform and the solution is saturated with dry hydrogen chloride and evaporated. The residue is crystallized from ethanol-diethyl ether to obtain the title compound as the dihydrochloridie salt; mp 280°-281° C.; ir (KBr) 3400, 2600 and 1640 cm$^{-1}$; uv(0.1 N HCl in MeOH) $\lambda_{max}$ 264,306 and 319 nm, ϵ=40000, 10300 and 11400, respectively; nmr (DMSO-d$_6$) δ1.2-2.3(m), 2.66(s), 2.8-4.0(m), 7.34(s), 7.55(m) and 8.15(m).

Anal. Calculated for C$_{24}$H$_{31}$N$_3$.2HCl: Cl, 16.30%. Found: Cl, 16.71%.

EXAMPLE 32

4-Methyl-5-[2-(1-piperidinyl)ethyl]-1-propyl-pyrimido[1,6-a]indole (I; $R^1$ and $R^3$=H, $R^2$=Pr, $R^4$=Me and $R^5$=1-piperidinyl)

A mixture of 5-(2-chloroethyl)-4-methyl-1-propyl-pyrimido[1,6-a]indole (3.9 g described in Example 15), piperidine (60 ml) and water (30 ml) is refluxed for 15 hours. The solution is evaporated to dryness and the residue is partition between chloroform and 10% ammonium hydroxide. The organic phase is washed with saturated brine, concentrated, and filtered through a column of neutral alumina packed in chloroform. The eluates are evaporated and the residue is crystallized from hexane to obtain the title compound (3.0 g): mp 79°-80° C.; nmr (CDCl$_3$) δ1.17(t), 1.35-2.25(m), 3.31(t) and 7.0-8.2(m).

The title compound is dissolved in diethyl ether and the solution is acidified with a solution of hydrogen chloride in diethyl ether and evaporated. The residue is crystallized from ethanol-diethyl ether to obtain the title compound as the dihydrochloride salt; mp 266°-267° C.; uv (MeOH) $\lambda_{max}$ 297, 309 and 328 nm; ϵ=7130, 8660 and 10200 respectively.

Anal. Calculated for C$_{22}$H$_{29}$N$_3$.2HCl: C,64.69; H,7.65; N,10.29%. Found: C,64.66; H,7.62; N,10.12%.

EXAMPLE 33

1-(N,N-Dimethylamino)-4-methyl-5-[2-(1-piperidinyl)ethyl]pyrimido[1,6-a]indole (I; $R^1$ and $R^3$=H, $R^2$=N(Me)$_2$, $R^4$=Me and $R^5$=1-piperidinyl)

A mixture of 5-(2-chloroethyl)-1-(N,N-dimethylamino)-4-methylpyrimido[1,6-a]indole (2.0 g, described in Example 16), piperidine (80 ml), and water (40 ml) is refluxed for 5 hours and evaporated. The residue is partitioned between chloroform and 5% ammonium hydroxide. The organic phase is dried over magnesium sulfate, filtered, concentrated, and applied on a silica gel column. Elution with chloroform gave the title compound (2.15 g), nmr (CDCl$_3$) δ1.67(m), 2.52(s), 2.65(m), 2.87(s), 3.39(t), 7.11(m), and 7.25-8.50(m).

The title compound is dissolved in diethyl ether and a solution containing two equivalents of maleic acid in diethyl ether is added. The solution is evaporated and the residue is crystallized from ethanol-diethyl ether to obtain the title compound as the dimaleate salt; mp 152°-154° C.; ir (nujol) 2500 and 1585 cm$^{-1}$; uv (MeOH) $\lambda_{max}$ 241, 282, 300, 310 and 323 nm; ϵ=38200, 7050, 5630, 9200 and 11660, respectively; nmr (DMSO-d$_6$): δ2.81 (s), 3.40 (m), 6.18 (s) and 7.1-8.4 (m). Anal. Calculated for C$_{21}$H$_{28}$N$_4$.2C$_4$H$_4$O$_4$: C,61.25; H,6.38; N,9.85%. Found: C,61.05; H,6.36; N,9.78%.

EXAMPLE 34

5-(2-Chloroethyl)-4-methyl-1-[(1-pyrrolidinyl)methyl]-pyrimido[1,6-a]indole (I; $R^1$ and $R^4$=H, $R^2$=(1-pyrrolidinyl)methyl, $R^4$=Me and $R^5$=Cl)

A mixture of 5-(2-chloroethyl)-1-chloromethyl-4-methylpyrimido[1,6-a]indole (293 mg, described in Example 17), pyrrolidine (78 mg), acetonitrile (30 ml), and sodium bicarbonate (200 mg) is stirred at 40° C. for 2 hours and evaporated to dryness. The residue is partitioned between water and chloroform and the organic phase is dried over magnesium sulfate, filtered, and evaporated to give the title compound (300 mg), nmr (CDCl$_3$) δ1.82(m), 2.55(d), 2.79(m), 3.66(m), 4.21(s), 7.23(d), 7.37(m), 7.70(m), and 8.10(m).

EXAMPLE 35

4-Methyl-5-[2-(1-pyrrolidinyl)ethyl]-1-[(1-pyrrolidinyl)methyl]pyrimido[1,6-a]indole (I; R$^1$ and R$^3$=H, R$^2$=(1-pyrrolidinyl)methyl, R$^4$=Me and R$^5$=1-pyrrolidinyl)

A mixture of 5-(2-chloroethyl)-1-chloromethyl-4-methylpyrimido[1,6-a]indole (3.0 g, described in Example 17) and pyrrolidine (50 ml) is refluxed for 10 hours and evaporated. The residue is stripped with benzene (200 ml) and partitioned between water and benzene. The organic phase is washed with 5% hydrochloric acid, and the aqueous part is rendered basic with sodium hydroxide and extracted with chloroform. The combined extracts are dried, filtered, and concentrated. The residue is chromatographed on alumina using chloroform and the eluates are evaporated to give the title compound (3.0 g), nmr (CDCl$_3$) δ1.86(m), 2.56(s), 2.70(m), 3.32(m), 4.12(s) and 7.05–8.25(m).

A solution of the title compound in chloroform is acidified with a solution of hydrogen chloride in diethyl ether and evaporated. The residue is crystallized from ethanol-diethyl ether to obtain the title compound as the dihydrochloride salt; mp 273°–274° C.; ir (nujol) 3380, and 2580 cm$^{-1}$; uv (MeOH) λ$_{max}$ 273, 283, 297, 308, and 323 nm; ε=8830, 6700, 4800, 7900, and 10400, respectively.

EXAMPLE 36

N-[1,4-Dimethyl-5-[2-(1-pyrrolidinyl)ethyl]-pyrimido[1,6-a]indol-3-yl]-4-oxo-4-(1-pyrrolidinyl)-butanamide (I; R$^1$=H, R$^2$ and R$^4$=Me, R$^3$=[4-(pyrrolidini-yl)-1,4-dioxobutyl]amino and R$^5$=1-pyrrolidinyl)

To a refluxing solution of 5-(2-chloroethyl)-1,4-dimethylpyrimido[1,6-a]indole (13 g, described in Example 12), in chloroform (400 ml) is added N-bromosuccinimide (9.4 g) and anhydrous potassium carbonate (7 g). The reaction mixture is stirred and refluxed for 45 minutes. The resulting slurry is cooled and washed with water, and the organic phase is separated and evaporated. The residue is chromatographed on silica gel using chloroform and the eluates are evaporated. The residue (6.6 g) is crystallized from ethyl acetate to give 1-[5-(2-chloro)ethyl-1,4-dimethylpyrimido[1,6-a]indol-3-yl]pyrrolidine-2,5-dione; mp 232°–234° C.; ir (CHCl$_3$) 1780 (weak) and 1705 cm$^{-1}$; uv (MeOH) λ$_{max}$ 299, 310, and 324 nm; ε=6300, 10180, and 13170, respectively; nmr (CDCl$_3$) δ2.31(s), 2.82(s), 2.91(s), 3.55(m), 7.0(m) and 8.0(m).

Anal. Calculated for C$_{19}$H$_{18}$ClN$_3$O$_2$: C,64.13; H,5.10; N,11.81%. Found: C,64.03; H,5.05; N,11.53%.

EXAMPLE 36 (continued)

A mixture of the latter compound (2.9 g) and pyrrolidine (20 ml) is heated at reflux for 6 hours. After cooling, an excess of pyrrolidine is removed under reduced pressure. The residue is taken up in benzene and washed with water. The product is extracted with 5% hydrochloric acid, and the aqueous phase is separated, basified with 10% sodium hydroxide and re-extracted with chloroform. The combined extracts are evaporated, and the crude product is chromatographed on a dry column of neutral alumina containing 5% of water. The column is developed in chloroform. The eluates are evaporated and the residue is triturated with diethyl ether and crystallized from benzene-hexane to obtain the title compound: mp 185°–187° C.; ir (CHCl$_3$) 3380, 3190, 1660 and 1600 cm$^{-1}$; uv (MeOH) λ$_{max}$ 254, 304, 315 and 328 nm; ε=40700, 7150, 11400, and 13140, respectively; nmr (CDCl$_3$) δ1.92(m), 2.48(s), 2.74(m), 2.99(s), 3.50(m), 7.25–8.15(m) and 8.56(s).

Anal. Calculated for C$_{27}$H$_{35}$N$_5$O$_2$: C,70.25; H,7.64; N,15.17%. Found: C,39.95; H,7.56; N,14.70%.

We claim:

1. A compound of formula I

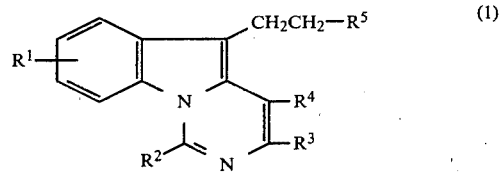

in which R$^1$ is hydrogen; R$^2$ is lower alkyl, cyclo(lower)alkyl, pyrrolidin-1-ylmethyl or a radical of formula —NR$^6$R$^7$ wherein R$^6$ and R$^7$ each is lower alkyl; R$^3$ is hydrogen, lower alkyl or [4-(pyrrolidin-1-yl)-1,4-dioxobutyl]amino; R$^4$ is lower alkyl; and R$^5$ is bromo, chloro, lower alkoxy, 1-pyrrolidinylthioxomethylthio, 4,5-dihydro-1H-imidazol-2-ylthio, or a radical of formula —NR$^{14}$R$^{15}$ wherein R$^{14}$ is lower alkyl and R$^{15}$ is lower alkyl, or hydroxy(lower)alkyl; or R$^{14}$ and R$^{15}$ together form a chain of formula —CH$_2$CH=CH—(CH$_2$)$_2$—, —(CH$_2$)$_2$—O—(CH$_2$)$_2$—, —(CH$_2$)$_4$—, —(CH$_2$)$_5$—, (CH$_2$)$_6$—, —(CH$_2$)$_2$—NR$^{16}$—(CH$_2$)$_2$— wherein R$^{16}$ is lower alkyl or 4-(lower alkoxy)phenyl, —(CH$_2$)$_2$—CHR$^{17}$—(CH$_2$)$_2$— wherein R$^{17}$ is benzoylamino, CH$_2$CHR$^{18}$OCHR$^{19}$CH$_2$ wherein R$^{18}$ and R$^{19}$ each is lower alkyl, or —CH=N—CH=CH—, or a therapeutically acceptable acid addition salt thereof.

2. A compound of formula I

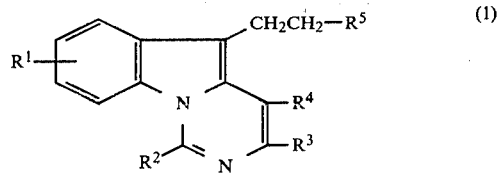

in which R$^1$ and R$^3$ are hydrogen; R$^2$ is lower alkyl, cyclo(lower)alkyl or pyrrolidin-1-ylmethyl; R$^4$ is lower alkyl; and R$^5$ is a radical of formula —NR$^{14}$R$^{15}$ wherein R$^{14}$ and R$^{15}$ each is lower alkyl or R$^{14}$ and R$^{15}$ together form a chain of formula —CH$_2$CH=CH—(CH$_2$)$_2$—, —(CH$_2$)$_2$—O—(CH$_2$)$_2$—, —(CH$_2$)$_4$—, —(CH$_2$)$_5$—, —(CH$_2$)$_2$NR$^{16}$—(CH$_2$)$_2$— wherein R$^{16}$ is lower alkyl or 4-(lower alkoxy)phenyl, or —(CH$_2$)$_2$—CHR$^{17}$—(CH$_2$)$_2$— wherein R$^{17}$ is benzoylamino, or a therapeutically acceptable acid addition salt thereof, as claimed in claim 1.

3. 5-(2-Chloroethyl)-1,4-dimethylpyrimido[1,6-a]indole, as claimed in claim 1.

4. 5-(2-Chloroethyl)-1-(N,N-dimethylamino)-4-methylpyrimido[1,6-a]indole, as claimed in claim 1.

5. 1,4-Dimethyl-5-[2-(methoxy)ethyl]pyrimido[1,6-a]indole, as claimed in claim 1.

6. 1,4,N,N-Tetramethylpyrimido[1,6-a]indole-5-ethanamine, as claimed in claim 1.

7. N,N-Diethyl-1,4-dimethylpyrimido[1,6-a]indole-5-ethanamine, as claimed in claim 1.

8. N-(1-Methylethyl)-1,4,N-trimethylpyrimido[1,6-a]indole-5-ethanamine, as claimed in claim 1.

9. 1,4,N-Trimethyl-N-(hydroxyethyl)pyrimido[1,6-a]indole-5-ethanamine, as claimed in claim 1.

10. 1,4-Dimethyl-5-[2-(1-pyrrolidinyl)ethyl]-pyrimido[1,6-a]indole, as claimed in claim 1.

11. 1,4-Dimethyl-5-[2-(1-piperidinyl)ethyl]-pyrimido[1,6-a]indole, as claimed in claim 1.

12. 1,4-Dimethyl-5-[2-(hexahydro-1H-azepin-1-yl)ethyl]pyrimido[1,6-a]indole, as claimed in claim 1.

13. 1,4-Dimethyl-5-[2-(1,2,5,6-tetrahydropyridin-1-yl)ethyl]pyrimido[1,6-a]indole, as claimed in claim 1.

14. 1,4-Dimethyl-5-[2-(4-morpholinyl)ethyl)ethyl]-pyrimido[1,6-a]indole, as claimed in claim 1.

15. 1,4-Dimethyl-5-[2-(2,6-dimethyl-4-morpholinyl)ethyl]pyrimido[1,6-a]indole, as claimed in claim 1.

16. 1,4-Dimethyl-5-[2-(4-benzoylamino-1-piperidinyl)ethyl]pyrimido[1,6-a]indole, as claimed in claim 1.

17. 1,4-Dimethyl-5-[2-[4-(4-methoxy)phenyl-1-piperazinyl]ethyl]pyrimido[1,6-a]indole, as claimed in claim 1.

18. 1,4-Dimethyl-5-[2-(4-methyl-1-piperazinyl)ethyl]-pyrimido[1,6-a]indole, as claimed in claim 1.

19. 1,4-Dimethyl-5-[2-(1H-imidazol-1-yl)ethyl]-pyrimido[1,6-a]indole, as claimed in claim 1.

20. 5-[2-(1-Pyrrolidinyl)ethyl]-1,3,4-trimethyl-pyrimido[1,6-a]indole, as claimed in claim 1.

21. 1-Cyclohexyl-4-methyl-5-[2-(1-pyrrolidinyl)ethyl]pyrimido[1,6-a]indole, as claimed in claim 1.

22. The monohydrochloride salt of 1-cyclohexyl-4-methyl-5-[2-(1-pyrrolidinyl)ethyl]pyrimido[1,6-a]indole, as claimed in claim 1.

23. The dihydrochloride salt of 1-cyclohexyl-4-methyl-5-[2-(1-pyrrolidinyl)ethyl]pyrimido[1,6-a]indole, as claimed in claim 1.

24. 4-Methyl-5-[2-(1-piperidinyl)ethyl]-1-propyl-pyrimido[1,6-a]indole, as claimed in claim 1.

25. 1-(N,N-Dimethylamino)-4-methyl-5-[2-(1-piperidinyl)ethyl]pyrimido[1,6-a]indole, as claimed in claim 1.

26. 4-Methyl-5-[2-(1-pyrrolidinyl)ethyl]-1-[(1-pyrrolidinyl)methyl]pyrimido[1,6-a]indole, as claimed in claim 1.

27. N-[1,4-Dimethyl-5-[2-(2-pyrrolidinyl)ethyl]-pyrimido[1,6-a]indol-3-yl]-4-oxo-4-(1-pyrrolidinyl)-butanamide, as claimed in claim 1.

28. 1-pyrrolidinecarbodithioic acid, β-(1,4-dimethyl-pyrimido[1,6-a]indol-5-yl)ethyl ester, as claimed in claim 1.

29. 5-[2-[(4,5-dihydro-1H-imidazol-2-yl)thio]ethyl]-1,4-dimethylpyrimido[1,6-a]indole, as claimed in claim 1.

30. A method of treating hypertension in a mammal, which comprises administering to said mammal an effective antihypertensive amount of a compound of formula I, or a therapeutically acceptable acid addition salt thereof, as claimed in claim 1.

31. A method of treating hypertension in a mammal, which comprises administering to said mammal an effective antihypertensive amount of a compound of formula I or a therapeutically acceptable acid addition salt thereof, as claimed in claim 2.

32. A method as claimed in claim 31 wherein said compound of formula I is 1-cyclohexyl-4-methyl-5-[2-(1-pyrrolidinyl)ethyl]pyrimido[1,6-a]indole or the monohydrochloride or dihydrochloride salt thereof.

33. An antihypertension pharmaceutical composition, which comprises a compound of formula I, or a therapeutically acceptable acid addition salt thereof, as claimed in claim 1, and a pharmaceutically acceptable carrier therefor.

34. An antihypertensive pharmaceutical composition, which comprises a compound of formula I, or a therapeutically acceptable acid addition salt thereof, as claimed in claim 2, and a pharmaceutically acceptable carrier therefor.

35. An antihypertensive pharmaceutical composition as claimed in claim 34 wherein said compound of formula I is 1-cyclohexyl-4-methyl-5-[2-(1-pyrrolidinyl)ethyl]pyrimido[1,6-a]indole or the monohydrochloride or dihydrochloride salt thereof.

* * * * *